United States Patent
Baum et al.

(10) Patent No.: US 11,752,085 B2
(45) Date of Patent: Sep. 12, 2023

(54) KERATIN-BASED HAIR STRAIGHTENING FORMULATIONS, METHODS AND SYSTEMS

(71) Applicant: BEAUTY BIOLABS LLC, Monrovia, CA (US)

(72) Inventors: Marc M. Baum, Pasadena, CA (US); Janelle M. Baum, Los Angeles, CA (US)

(73) Assignee: BEAUTY BIOLABS LLC, Monrovia, CA (US)

( * ) Notice: Subject to any disclaimer, the term of this patent is extended or adjusted under 35 U.S.C. 154(b) by 0 days.

(21) Appl. No.: 16/595,191

(22) Filed: Oct. 7, 2019

(65) Prior Publication Data
US 2020/0046626 A1    Feb. 13, 2020

Related U.S. Application Data

(63) Continuation of application No. 14/003,758, filed as application No. PCT/US2012/028444 on Mar. 9, 2012, now Pat. No. 10,434,053.

(60) Provisional application No. 61/464,683, filed on Mar. 9, 2011.

(51) Int. Cl.
| | | |
|---|---|---|
| *A61K 8/65* | (2006.01) | |
| *A61K 8/36* | (2006.01) | |
| *A61K 8/365* | (2006.01) | |
| *A61K 8/44* | (2006.01) | |
| *A61K 8/46* | (2006.01) | |
| *A61K 8/49* | (2006.01) | |
| *A61K 8/55* | (2006.01) | |
| *A61Q 5/04* | (2006.01) | |
| *A61K 8/67* | (2006.01) | |
| *A61K 8/20* | (2006.01) | |
| *A61K 8/9789* | (2017.01) | |
| *A61K 8/9794* | (2017.01) | |
| *A45D 7/06* | (2006.01) | |
| *A45D 2/00* | (2006.01) | |
| *A45D 7/04* | (2006.01) | |
| *A61K 8/04* | (2006.01) | |
| *A61K 8/34* | (2006.01) | |
| *A61K 8/41* | (2006.01) | |
| *A61K 8/891* | (2006.01) | |

(52) U.S. Cl.
CPC ............ *A61K 8/65* (2013.01); *A45D 2/001* (2013.01); *A45D 7/04* (2013.01); *A45D 7/06* (2013.01); *A61K 8/042* (2013.01); *A61K 8/20* (2013.01); *A61K 8/342* (2013.01); *A61K 8/345* (2013.01); *A61K 8/36* (2013.01); *A61K 8/365* (2013.01); *A61K 8/416* (2013.01); *A61K 8/44* (2013.01); *A61K 8/442* (2013.01); *A61K 8/46* (2013.01); *A61K 8/49* (2013.01); *A61K 8/4913* (2013.01); *A61K 8/55* (2013.01); *A61K 8/676* (2013.01); *A61K 8/891* (2013.01); *A61K 8/9789* (2017.08); *A61K 8/9794* (2017.08); *A61Q 5/04* (2013.01); *A61K 2800/884* (2013.01)

(58) Field of Classification Search
None
See application file for complete search history.

(56) References Cited

U.S. PATENT DOCUMENTS

| | | |
|---|---|---|
| 5,061,483 A | 10/1991 | Tieckelmann et al. |
| 6,488,920 B1 | 12/2002 | Thomas |
| 6,984,250 B1 | 1/2006 | Legrand et al. |
| 7,148,327 B2 | 12/2006 | Kelly et al. |
| 2003/0066141 A1 † | 4/2003 | Oshika |
| 2003/0106168 A1 † | 6/2003 | Tian |
| 2005/0118124 A1 † | 6/2005 | Reinhart |
| 2006/0024257 A1 | 2/2006 | Chang et al. |
| 2006/0127337 A1 | 6/2006 | Radisson |
| 2007/0028938 A1 | 2/2007 | Tiwari |
| 2007/0048235 A1 | 3/2007 | Harmalker et al. |
| 2009/0074683 A1 † | 3/2009 | Van Nguyen |
| 2009/0126756 A1 * | 5/2009 | Syed .................. A61Q 5/04 132/209 |
| 2009/0165812 A1 † | 7/2009 | Resnick |
| 2009/0252697 A1 | 10/2009 | Barbarat et al. |
| 2010/0196302 A1 | 8/2010 | Vermelho et al. |
| 2011/0105623 A1 * | 5/2011 | Benjamin ............ A01N 41/10 514/711 |

FOREIGN PATENT DOCUMENTS

| | | | |
|---|---|---|---|
| KR | 20030003970 | † | 1/2003 |
| KR | 1020060059564 | † | 6/2006 |

(Continued)

OTHER PUBLICATIONS

National Center for Biotechnology Information, "PubChem Compound Summary for CID 444266, Maleic Acid," PubChem, https://pubchem.ncbi.nlm.nih.gov/compound/Maleic-acid.

"Straight Hair Essence", Margaret Josefin, Product Information (Apr. 2010).

EP Application No. 12754671.1 Extended European Search Report dated Oct. 9, 2015, 4 pages.

European Application No. 12754671.1, Communication Pursuant to Article 94(3) EPC, dated Apr. 21, 2017.

(Continued)

*Primary Examiner* — David J Blanchard
*Assistant Examiner* — Sarah J Chickos
(74) *Attorney, Agent, or Firm* — MARSHALL, GERSTEIN & BORUN LLP

(57) ABSTRACT

The present invention teaches a hair straightening system including formulations that will safely and effectively straighten curly hair for at least 2-3 months after a single application, despite frequent washings of the hair. Methods for obtaining said formulations are disclosed. Hair straightening systems including shampoo and one or more conditioners are also provided.

28 Claims, No Drawings

(56) References Cited

FOREIGN PATENT DOCUMENTS

| WO | WO-2007/032762 A1 | 3/2007 |
| WO | WO-2012122457 A2 | 9/2012 |

OTHER PUBLICATIONS

Hall et al., Application of the Theory of Hydrophobic Bonds to Hair Treatments, Journal of the Society Cosmetic 3hemists, 1977, vol. 28(5), pp. 231-241.
IPRP for PCT/US2012/028444,1 page.
ISR for PCT/US2012/028444, 2 pages.
Written Opinion for PCT/US2012/028444, 5 pages.
U.S. Office Action for U.S. Appl. No. 15/043,376, dated Oct. 26, 2018.
U.S. Office Action for U.S. Appl. No. 15/043,376, dated Sep. 21, 2017.
U.S. Office Action for U.S. Appl. No. 15/043,376, dated Apr. 22, 2016.
U.S. Office Action for U.S. Appl. No. 15/043,376, dated Apr. 19, 2018.
U.S. Office Action for U.S. Appl. No. 15/043,376, dated Sep. 23, 2016.

\* cited by examiner
† cited by third party

KERATIN-BASED HAIR STRAIGHTENING FORMULATIONS, METHODS AND SYSTEMS

CROSS-REFERENCE TO RELATED APPLICATIONS

This application is a continuation of U.S. patent application Ser. No. 14/003,758, filed Sep. 9, 2013, which is a National Stage Entry of International Patent Application No. PCT/US12/28444, filed Mar. 9, 2012 which claims priority from U.S. Provisional Patent Application No. 61/464,683, filed on Mar. 9, 2011, all of which are incorporated herein by reference in their entirety.

FIELD OF INVENTION

The present invention relates to keratin-based hair straightening formulations, methods and systems.

BACKGROUND

All publications referenced herein are incorporated by reference to the same extent as if each publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Hair is a filamentous biomaterial that grows from follicles found in the dermis. Human hair has many textures, from fine to coarse, and from straight to curly. The outermost layer of the hair filament is called the cuticle and consists of translucent scales that cover the shaft. The cuticle protects the shaft from environmental damage. It is also sensitive to pH changes: at high pH the scales open, leaving the cortex exposed to environmental conditions. This is commonly exploited in hair processing, from straightening to coloring. Hair is composed primarily (around 88%) of keratin, a protein made up of chains of polypeptide helix coils. The polypeptides have a high cystine content that leads to extensive crosslinking via the disulfide linkage. The bonds are perpendicular to the helix coils, with one bond for every four turns of the helix. It is the crosslinking that gives hair its toughness and abrasion resistance, as well as defining its shape.

Curly hair is made of hair strands with irregular surfaces that mesh and tangle to make combing and management more challenging than with straight hair. It therefore has become popular among many individuals to relax or straighten hair in order to increase manageability and ease of styling.

The oldest form of hair straightening involves the use of strongly alkaline agents, at pH 12-14, to permanently convert the crosslinking disulfide bonds in cystine to lanthionine. During this harsh chemical treatment, the hair is mechanically maintained in a straight conformation. In a milder, alternative hair relaxation process, the cystine disulfide bonds are chemically reduced to produce temporary cysteine residues. Common reducing agents used in these processes include thioglycolic acid, ammonium thioglycolate, and bisulfite. These are typically used at high pH (e.g., 9.5). A neutralizer/fixative is applied in the second stage of the treatment, along with mechanical straightening and flat-ironing at 200° C. (400° F.), to restore the pH balance to the hair and to re-form the disulfide crosslinks in their new positions. This process produces permanent straightening, is damaging to the hair, and takes a relatively long time (4-6 hours) to perform.

The demand for temporary (1-6 months) hair straightening systems that remove the frizz from curly or wavy hair leading to a straighter form without the use of harsh chemicals has grown in recent years. The popular temporary hair straightening process known as escova progressiva was pioneered in Brazil. Known in the United States as "Brazilian hair straightening" or "keratin straightening," this process can provide results lasting up to 5 months and uses high temperatures (typically 230° C., 450° F.), keratin lysate, and elevated levels (1-5%) of formaldehyde as its primary components. The highly toxic nature of formaldehyde, a proven human carcinogen, and the high temperatures used in the process raise legitimate concerns regarding its safety for stylists and clients. Other, similar treatments have emerged that replace the toxic formaldehyde with chemicals such as glyoxal. For example, Resnick et al. disclose a formulation and method relying on keratin lysate, a crosslinking agent such as a polyfunctional aldehyde, and styling with a flat iron to achieve curl minimization (1). This treatment, however, has the disadvantage of requiring high levels of heat (typically >200° C.) to be effective, and these high temperatures often cause an undesirable change in color of the processed hair (e.g., orange coloring). Syed et al. also discloses a curl minimizing composition based on keratin lysate, a crosslinking agent, and heat to achieve temporary hair straightening (2). However, that treatment, as described, is unlikely to achieve sustained hair straightening lasting in excess of several months with repeated hair washing. Considering the practical limitations and safety concerns relating to existing hair straightening treatments and methods, there is clearly a need in the art for a more effective and non-toxic means of hair straightening.

SUMMARY OF THE INVENTION

In some embodiments, the invention teaches a method for straightening a quantity of hair, including: providing one or more pH-lowering agents; providing one or more reducing agents; and applying the one or more pH-lowering agents and the one or more reducing agents to the quantity of hair. In some embodiments, the method further includes applying one or more crosslinking agents and/or one or more keratin protein fractions to the quantity of hair. In some embodiments, the method further includes applying to the quantity of hair one or more substances selected from the group consisting of amino acids, botanicals, surfactants, emollients, emulsifiers, skin-cleaning agents, preservatives, fragrances, pre-conditioners, thermal protectants, and aqueous-based diluents. In some embodiments, one or more of the pH lowering agents and reducing agents are applied to the quantity of hair separately. In some embodiments, one or more of the pH lowering agents, reducing agents, crosslinking agents and/or keratin protein fractions are applied to the quantity of hair separately. In some embodiments, the quantity of hair is substantially dry when the one or more pH lowering agents and/or the one or more reducing agents are applied to the quantity of hair. In some embodiments, the quantity of hair is substantially dry when the one or more pH lowering agents, reducing agents, crosslinking agents and/or keratin protein fractions are applied to the quantity of hair. In some embodiments, the quantity of hair is wet when the one or more pH lowering agents and/or the one or more reducing agents are applied to the quantity of hair. In some embodiments, the quantity of hair is wet when the one or more pH lowering agents, reducing agents, crosslinking agents and/or keratin protein fractions are applied to the quantity of hair. In some embodiments, the method further includes washing the quantity of hair with a shampoo no more than three hours prior to applying the one or more pH lowering agents and reducing agents. In some embodiments, the method further includes applying a straightening iron to the quantity of hair.

In certain embodiments, the invention teaches a hair straightening composition, including a quantity of one or more pH lowering agents and quantities of two or more substances selected from the group consisting of reducing agents, crosslinking agents, and keratin protein fractions.

In some embodiments, the composition further includes one or more substances selected from the group consisting of amino acids, botanicals, surfactants, emollients, emulsifiers, skin-cleaning agents, preservatives, fragrances, preconditioners, thermal protectants, and aqueous-based diluents. In some embodiments, one or more of the pH-lowering agents includes an organic acid. In some embodiments, the organic acid is a naturally-occurring organic acid. In certain embodiments, the pH lowering agent is an aliphatic or aromatic mono-carboxylic acid or a poly-carboxylic acid. In certain embodiments, the pH lowering agent is selected from the group consisting of formic acid, acetic acid, propionic acid, tartaric acid, adipic acid, succinic acid, ascorbic acid, malonic acid, oxalic acid, pyruvic acid, picolinic acid, dipicolinic acid, citric acid, and combinations thereof. In some embodiments, one or more of the reducing agents are capable of breaking at least a portion of the S—S bonds in human hair when applied to said human hair. In some embodiments, one or more of the reducing agents is organic. In some embodiments, one or more of the reducing agents is selected from the group consisting of naturally-occurring amino acids, non-naturally-occurring amino acids, members of the thiazoline family, members of the 2-mercapto-ethane family, dithiothreitol (DTT), tris(2-carboxyethyl)phosphine (TCEP), tris(2-carboxyethyl)phosphine-HCl (TCEP-HCl), sulfamic acid, sulfamates, $FeCl_2$, and combinations thereof. In some embodiments, one or more of the reducing agents lowers the pH of the hair straightening composition. In some embodiments, one or more of the reducing agents is selected from the group consisting of cysteine-HCl, ascorbic acid, 2-mercaptoethylamine-HCl, sulfamic acid, and $FeCl_2$. In some embodiments, one or more of the reducing agents is an antioxidant. In some embodiments, one or more of the reducing agents is ascorbic acid. In some embodiments, one or more of the crosslinking agents is a non-formaldehyde aldehyde. In some embodiments, one or more of the crosslinking agents includes one or more substances selected from the group consisting of monofunctional aldehydes, polyfunctional aldehydes, ketones, hydroxyketones, ketoaldehydes, activated olefin-containing compounds, polycarboxylic acids, mono-epoxy compounds, poly-epoxy compounds, carbonates, imidoesters, carbodiimides, hexamethylene diisocyanate, N-hydroxysuccinimide esters, haloacetyls, pyridyl disulfide, hydrazides, aryl azides, and combinations thereof. In some embodiments, the composition further includes a Lewis acid catalyst.

In some embodiments, the invention teaches a kit for straightening a quantity of hair, including: a hair straightening composition described herein; and instructions for the use thereof for straightening the quantity of hair. In some embodiments, the kit further includes a shampoo, a conditioner, a flat iron, a hair dryer, one or more disposable gloves, a brush, and/or a comb.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. March, *Advanced Organic Chemistry Reactions, Mechanisms and Structure.* $5^{th}$ ed., J. Wiley & Sons (New York, N.Y. 2001); *International Cosmetic Ingredient Dictionary and Handbook.* 9th ed.; Cosmetic, Toiletry, and Fragrance Association: Washington D.C., 2002; Vol. 1-3; 2001 *McCutcheon's Directories.* McCutcheon's Division. The Manufacturing Confectioner Publishing Co.: Glen Rock, N.J., 2001; Vol. 1-2; and DiBerardino, L., *CBR Cosmetic Bench Reference—Directory of Cosmetic Ingredients* 2005. Cosmetics and Toiletries, Allured Publishing Corporation: Carol Stream, Ill., 2005, together provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For the purposes of the present invention, the following terms are defined below.

As used herein, the terms "solution," "preparation," "composition" and "formulation" can be used interchangeably. The terms "modulates hair frizz," "defrizzes hair" and "curl minimizing" are used interchangeably. As defined herein. "modulates" hair frizz means that it either reduces or prevents hair frizz. The term "curl minimizing agent," as used herein, refers to compounds disclosed herein capable of forming a covalent bond or crosslink with a protein end group in human hair keratin, when applied thereto by an aqueous vehicle. The term "heat-assisted," as used herein, refers to the use of a frizz minimizing composition of the present invention in conjunction with a heating device, such as an electrically heated flat hair iron or hair dryer, at some point in the process.

Hand-held hair dryers are conventionally used to "blow dry" hair, preferably using an ambient heat setting temperature in the range of about 100° C. to about 108° C., more preferably in the range of about 105° C. to about 106° C. Commercial electric flat hair irons are available having variable heat settings, and preferably are ceramic, heated to platen temperatures in the range of about 100° C. to about 240° C., more preferably in the range of about 150° C. to about 235° C.

The term "temporary straightening" means that the frizz modulating effect resists reversion to the natural curl configuration on being subjected to more than one washing, preferably at least four washings, and more preferably at least eight washings, or the effect lasts until the scalp hair grows sufficiently to visibly warrant another frizz reducing procedure. The terms "washed" and "washing" include rinsing with water, shampooing or a combination of rinsing with water and shampooing. The terms "precondition," "preconditioning," and grammatical variations thereof, as used herein, refer to compositions containing conditioners that are applied to the hair in a first step of a multi-step curl minimizing process, and to hair that has been so conditioned. As defined herein. "leave-in" conditioner is a conditioner that is applied to hair and is not removed by rinsing.

The terms "keratin-protectant" and "hair protectant" are used interchangeably as applied to a curl minimizing composition of the present invention and refer to allowing for the retention of at least one discernible desirable characteristic, such as strength, sheen, smooth tactile character, and retention of original, natural hair color or tone, and the like, that is conventionally associated with the physical, mechanical integrity of natural hair keratin before receiving a curl minimizing procedure with the composition, and, in particular, before receiving a heat-assisted, curl minimizing procedure of this invention. The term "isoelectric point" is defined as the pH at which a particular molecule, polymer, or surface carries no net electrical charge. The term "reducing agent" is used herein to refer to any chemical agent that, under the conditions described herein, can chemically reduce the S—S bond in cystine residues inherent in the proteins contained in human hair. The term "crosslinker" is defined as one or more chemical agents that can forms crosslinks with at least one protein end group in hard keratin, such as human hair keratin or wool. For example, formaldehyde can form crosslinks between NH, OH, and SH groups in such proteins. The term "polyfunctional aldehyde" means more than one aldehyde is present in the compound, such as a dialdehyde, a trialdehyde, and the like.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Keratin-protectant, curl minimizing compositions and processes of the present invention avoid the deleterious action that can be caused by conventional highly alkaline lanthionization chemical hair relaxer processes, manifested as measurable changes in the physical, chemical, and mechanical integrity of the keratin fibers. Measurable changes in the integrity of the hair include changes in tensile strength properties, elasticity, porosity, cuticle erosion, fiber breakage, wet and dry combing force and the like, as well as changes in discernible subjective properties, i.e., tactile feel, and visible sheen or appearance.

Hard keratin fibers, such as human hair and wool, have a complex morphological structure and are predominantly proteinaceous. The proteins in human hair, for example, are polymers made up of a number of amino acids, and the linkages of the amino acids and peptide bonds are responsible for the strength of the protein backbone. Hair fibers are quite strong, and strength is conferred on the fiber by the inner cortex and protective outer cuticle sheath. The main bulk of the fiber, the cortex, consists essentially of long coiled peptide chains joined in one plane by salt and sulfur linkages, and in the other plane by hydrogen bonds. The chemical structure of hair keratin makes it susceptible to attack by chemical reagents. Hair keratin is more susceptible to alkaline hydrolysis than to acid hydrolysis (3).

Naturally occurring covalent crosslinks in hair keratin contribute to the physical stability and mechanical strength of the fibers. Some naturally occurring covalent crosslinks in the hair include: disulfide (cystine) bonds formed between two cysteine residues in either the same protein chain or adjacent protein chains; isopeptide bonds formed as amide crosslinks in the follicle; and peptide bonds existing between the amino groups of lysine and the carboxyl groups of aspartic acid or glutamic acid in portions of the same polypeptide chain or between different polypeptide chains. The tensile properties of wet keratin fibers are related to the presence of disulfide bonds and the tensile properties of dry keratin are influenced by the peptide bonds. The presence of crosslinks in human hair introduced by chemical reagents has been measured in the art directly by analytical techniques, and indirectly, based on changes in the mechanical strength and/or physical stability of the fiber measured instrumentally or quantitatively from such fiber properties as swelling, sorption, super contraction, setting, tensile strength, weight gain, alkali solubility and the like.

The reaction between hair and chemical reagents is generally complex and more than one type of linkage is affected. Naturally-occurring sites and linkages that are susceptible to reaction with simple chemical reagents, for example, include hydrogen bonds and van der Waals forces between adjacent peptide chains and side chains of the alpha-keratin-fibers, and salt linkages that can be reversibly fissioned by acids or short time exposure to base. Temporary hair styles that rely on bonding through salt linkages and hydrogen bonds typically are broken by exposure to water and humidity resulting in loss of temporary hair set, typically seen as reversion of a hair style set to its natural configuration, i.e., revert to a curly state (rekink or frizz) or uncurl to a naturally straight state.

Bearing in mind all of the above-described properties of hair, and its responses to various chemical treatments, the inventors developed new and improved formulations, systems and methods for straightening hair.

The present invention teaches a novel approach to keratin-based hair straightening based upon the integration of three key synergistic components, including: (1) adjusting the pH of hair to a value close to its isoelectric point; (2) chemically reducing the disulfide bonds in the keratin proteins making up hair fibers; and (3) chemically crosslinking reactive groups in the keratin proteins making up hair fibers as well as between reactive groups in the keratin proteins making up the hair fibers and proteins in the keratin lysate included in the formulations disclosed herein.

The novel approach set forth herein results in the following significant advantages, among others: (1) efficient curl-minimization with reduced frizz for periods lusting up to five months or longer; (2) avoidance of highly toxic formaldehyde, or formaldehyde precursors, in the crosslinking step; and (3) lowering of the processing temperature to below the 232° C. (450° F.) typically used in other keratin curl-minimizing treatments, resulting in less damage to the hair.

Formulations, methods, and systems based on the approach described above are disclosed in detail below.

Isoelectric Point Adjusting Agents

Hair comprises proteins and proteins are characterized, among other things, by an isoionic point and an isoelectric point (4). The isoionic point is the pH value at which the number of total positive charges on a protein is equal to the number of total negative charges. The isoionic point of hair is about equal to pH 6.0. The isoelectric point is a surface property of solid proteins and is that pH value at which the number of positive charges on the surface of the protein equals the number of negative charges. The isoelectric point of human hair normally is about pH 3.7. The exact value for individual hair can vary slightly from this value, and investigators differ on the range of isoelectric point pH values; pH 3.3 to 4.5 and more recently pH 2.45 to 3.17 (5, 6). In any case, at the isoelectric point, protein carries a neutral charge. An advantage is gained from inducing hair protein keratin to gather a neutral ionic charge, that is, to treat hair at its isoelectric point. At its isoelectric point, a protein displays its greatest insolubility and greatest ionic stability against chemical reactions. Hair treated at its isoelectric point pH, so that its protein can acquire an uncharged neutral state, is likely rendered stronger than hair treated at other pHs. Accordingly, the curl minimizing preparation of the present invention preferably contains at least one buffer substance or a buffer system, which has buffer capacity in a range of about pH 2.0 to 7.0, and especially includes the isoelectric point of human hair, as described herein.

In various embodiments of the present invention, one or more substances are used to lower the pH to approximately the above-referenced range. In some embodiments, one or more of the substances used to lower the pH of the formulation to the above-referenced range are selected from the group consisting of: formic acid, acetic acid, propionic acid, other aliphatic or aromatic mono- or poly-carboxylic acids, and combinations thereof. In some embodiments of the present invention, one or more organic acids are used to lower the pH of the formulations disclosed herein to about 3.0-4.5. In certain embodiments, one or more of the organic acids are selected from the group consisting of: tartaric acid, adipic acid, succinic acid, ascorbic acid, malonic acid, oxalic acid, pyruvic acid, picolinic acid, dipicolinic acid, citric acid, and combinations thereof. In certain embodiments, a plurality of acids is used as a mixture.

Reducing Agents

Reducing agents used in various embodiments of the present invention must be compatible with the above-described pH range, which excludes those in the thioglycolate family typically used in the art for this purpose.

In certain embodiments, one or more of the reducing agents include natural and/or non-natural amino acids that are sufficiently electrochemically reducing under the conditions of the curl minimizing treatment described herein to break the S—S bonds in human hair. In certain embodiments, the amino acids are selected from the group consisting of: cysteine, cysteine-HCl, methionine, methionine-HCl, and combinations thereof. In certain embodiments, the reducing agents are members of the thiazoline family. In some embodiments, the members of the thiazoline family used herein are selected from the group consisting of: thiazoline, thiazolidine carboxylic acid, and combinations thereof. In various embodiments of the present invention, the reducing agent is a member of the 2-mercapto-ethane family. In some embodiments, members of the 2-mercapto-ethane family are selected from the group consisting of: 2-mercaptoethanol, 2-mercaptoethylamine, and 2-mercaptoethylamine-HCl. In yet other embodiments of the invention, the reducing agent consists of dithiothreitol (DTT). In certain embodiments of the present invention, the reducing agent is selected from the group consisting of: tris(2-carboxyethyl)phosphine (TCEP) and tris(2-carboxyethyl)phosphine-HCl (TCEP-HCl). In certain embodiments, one or more of the reducing agents consists of sulfamic acid. In certain embodiments, one or more of the one or more reducing agents is a sulfamate. In certain embodiments, the sulfamate is selected from the group consisting of: O-substituted-, N-substituted-, and di-/tri-substituted derivatives of sulfamic acid.

In certain embodiments of the present invention, one or more of the reducing agents is organic and has antioxidant properties. In certain embodiments, the reducing agent with antioxidant properties is ascorbic acid.

In some embodiments of the present invention, one or more of the reducing agents used consists of an inorganic salt. In certain embodiments, the inorganic salt is iron (II) chloride ($FeCl_2$).

In some embodiments, one or more of the reducing agents used herein also lower the pH of the formulation. In some embodiments, these reducing agents are selected from the group consisting of: cysteine-HCl, ascorbic acid, 2-mercaptoethylamine-HCl, sulfamic acid, $FeCl_2$, and combinations thereof.

As disclosed above, in various embodiments a plurality of reducing agents are used as a mixture.

Crosslinking Agents

The keratin-protectant, curl minimizing compositions of the present invention employ one or more curl minimizing agents that can form crosslinks with protein end groups in naturally curly keratin to achieve hair styles having a decreased bulk in hair volume by loosening or straightening fiber alignment. The Keratin-protectant, curl minimizing compositions of the present invention contain an effective quantity of at least one physiologically tolerable curl minimizing agent that is capable of forming crosslinks with at least one protein end group in hard keratin. In some embodiments, the hard keratin is selected from the group consisting of: human hair keratin, animal hair keratin, and wool. Certain embodiments described herein are for use on human hair keratin.

The highly toxic aldehyde, formaldehyde, or chemicals that release formaldehyde upon heating such as paraformaldehyde are expressly excluded from certain embodiments of the present invention. In other embodiments, the formulations disclosed herein are substantially free of formaldehyde.

In certain embodiments of the present invention, one or more of the one or more crosslinking agents include one or more monofunctional non-formaldehyde aldehydes. In various embodiments, the crosslinking agents are selected from the group consisting of: benzaldehyde, butanal, propanal, cinnamaldehyde, and salicylaldehyde. Other embodiments include chemicals selected from vanillin, glyceraldehyde and the like, present in physiologically tolerable amounts. In some embodiments, these crosslinking agents are about 0.1-3.0% on a total composition weight basis. In some preferred embodiments, these crosslinking agents are in the range of about 0.15-2.0% on a total composition weight basis. In other preferred embodiments, these crosslinking agents are in the range of about 0.2-0.5%, on a total composition weight basis.

In certain embodiments, one or more of the one or more aldehydes are dialdehydes. In some embodiments, the dialdehydes are selected from the group consisting of: glutaraldehyde, glyoxal, glycolaldehyde dimer, and adipaldehyde. In some embodiments, these crosslinking agents are about 0.1-3.0% on a total composition weight basis. In some preferred embodiments, these crosslinking agents are in the range of about 0.15-2.0% on a total composition weight basis. In other preferred embodiments, these crosslinking agents are in the range of about 0.2-0.5%, on a total composition weight basis.

While not wishing to be bound by any one particular theory, it is very likely that one or both functional groups of dialdehydes can react with protein end groups to advantageously produce a more complex, more crosslinked protein-aldehyde product with a higher molecular weight that is more stable (i.e., less readily hydrolyzed) than complexes formed by the monofunctional aldehyde formaldehyde.

In certain embodiments, glutaraldehyde is used in combination with hydrolyzed polyvinyl alcohol (PVA). While not wishing to be bound by any one particular theory, PVA reportedly reacts with glutaraldehyde by acetalization to form a bulky pentane dilated PVA having highly reactive aldehyde, hemiacetal, and acetal groups available for reaction with the amino acids of hair containing OH groups, such as serine, tyrosine and threonine, to form a crosslinking network. The reported percentage of serine in hair is relatively high (11.5%) and hence serine can be easily targeted for crosslinking. In these embodiments, any free PVA present in the hair which has not reacted with the dialdehyde can remain in the matrix of the fiber and further help in straightening due to its high molecular weight. Furthermore, free glutaraldehyde left after the acetalization reaction is also available to crosslink the hair.

In certain embodiments, one or more of the one or more crosslinkers is a ketone. In certain embodiments, the crosslinkers include hydroxyketones and/or ketoaldehydes. In certain embodiments, one or more of the one or more crosslinkers are selected from the group consisting of: hydroxyacetone, pyruvaldehyde, pyruvic acid, combinations thereof and the like.

In some embodiments, the present invention teaches combinations of one or more of the crosslinkers with a Lewis acid catalyst. In some embodiments, the Lewis acid catalyst is selected from the group consisting of: zinc nitrate ($Zn(NO_3)_2$), magnesium chloride ($MgCl_2$), iron chloride ($FeCl_2$ or $FeCl_3$), and the like. Polyfunctional aldehydes can react with hydroxyl groups to form a hemiacetal, which can be catalyzed by a Lewis acid to form a stabilized acetal.

Because the crosslinking effect is mediated by the Maillard Reaction and cross-linking of the keratin fibers, in some embodiments, other Maillard reactants and cross-linking agents are substituted for the above aldehydes. In some embodiments, the chemical cross-linking effect involves sugars, including dihydroxyacetone, acetones and ethers that undergo the Maillard reaction.

In some embodiments, the invention discloses an activated olefin-containing substance having at least one double bond bearing at least one electron withdrawing substituent, such as, without limitation, a carboxylic acid, an ester, an amide, an imide, a nitrile, or an anhydride. In some embodiments, the physiologically tolerable, activated olefin-containing substance is substantially non-irritating to human skin; substantially chemically stable in the composition medium; and does not itself impart, or contribute to, any visibly undesirable coloration on the hair or skin. In some embodiments disclosed herein, activated olefin-containing substances include one or more chemicals selected from the group consisting of: maleic acid, esters of maleic acid, maleimides, N-substituted derivatives of maleimides, maleamic acid, N-substituted derivatives of maleamic acid, maleic anhydride, and combinations thereof. Preferred N-substituents are N—($C_1$-$C_{20}$)-alkyl, N-aryl, and N-haloaryl. In certain embodiments, maleic acid derivatives are used. In some embodiments, the maleic acid derivatives are maleimides. Advantageously, maleimides are known to undergo nucleophilic addition reactions with thiol groups in wool, and also crosslink amine, hydroxyl, and amide groups.

In some embodiments, the present invention teaches the use of mono-esters of maleic acid. In some embodiments, mono-ester is a poly($C_2$-$C_4$)-alkylene glycol ester. In certain embodiments, the polyalkylene glycol ester is selected from the group consisting of: polyethylene glycol esters, polypropylene glycol esters, polybutylene glycol esters, and combinations thereof. In preferred embodiments, the polyethylene glycol ester is a polyalkylene glycol bis-maleinate, sold commercially as a water miscible, medium-viscosity, liquid under the trade name MIRALAN™ HTP, by Ciba Specialty Chemicals Corporation. According to the supplier's data sheets, MIRALAN™ HTP contains about 65 to about 75% by weight poly(oxy-1,2-ethanediyl)-alpha-hydro-omega-hydroxy, (2Z)-2-butenedioate corresponds to CAS Number 37310-95-5, has a pH in the range of about pH 2 (5% solution) to about pH 2.7 (1 gram/liter), and is reportedly anionic in character.

In certain embodiments. N-substituted maleimide derivatives are used in the present invention. In some embodiments, the N-substituted maleimide derivative is N-naphthylmaleimide or N-trifluorophenylmaleimide. An exemplary N-substituted maleamic acid derivative is N-trifluorophenylmaleamic acid.

In certain embodiments, a polycarboxylic acid is used as one or more of the crosslinkers. In some embodiments, one or more of the polycarboxylic acids are selected from the group consisting of: oxalic acid, malonic acid, tartaric acid, dipicolinic acid, 1,2,3,4-butanetetracarboxylic acid (BTCA), 1,2,3,4-cyclopentanetetracarboxylic (CPTA), citric acid, polyacrylic acid, and the like. In certain embodiments, the invention discloses a combination of a polycarboxylic acid and cyclodextrin. In some embodiments, the invention discloses the combination of BTCA and cyclodextrin. Advantageously, this combination reportedly forms a copolymer that can crosslink through amide groups, based on studies with wool. In some embodiments, the invention discloses the use of esters of one or more of the above polycarboxylic acids. In some embodiments, the esters include dimethyl oxalate and dimethyl malonate. In certain embodiments, these crosslinkers are used in a range of about 1.0-25.0% on a total composition weight basis. In preferred embodiments, these crosslinkers are used in a range of about 5.0-20.0% on a total composition weight basis.

In certain embodiments of the present invention, one or more epoxy-type crosslinkers are used. In some embodiments, the epoxy-type crosslinkers include styrene oxide and/or epihalohydrins. In some embodiments, the epoxy-type crosslinkers include epichlorohydrin and/or epibromohydrin. In a preferred embodiment the epoxy crosslinker is epichlorohydrin. In some embodiments, the invention discloses the use of diepoxides as crosslinkers. In some embodiments, the crosslinkers are 1,4-butanediol-diglycidyl ethers. In some embodiments, the one or more crosslinkers are precursors of epihalohydrins and diepoxides. In certain embodiments, the precursors are selected from the group consisting of: 1,3-dichloropropanol-2 and 1,4-dichloro-2,3-dihydroxybutane.

In some embodiments, the present invention discloses the use of polyepoxy compounds that are sometimes used as collagen crosslinking agents (7-8). At least some of these known polyepoxy fixatives are commercially available under the trademark Denacor™ from Nagase Chemicals, Ltd., Osaka, Japan. In particular, one difunctional epoxy compound which has been used as a collagen crosslinking agent is an ethylene glycol diglycidyl ether based compound commercially available from Nagase Chemicals, Ltd. of Osaka. Japan under the designation Denacol Ex-810. Other epoxy compounds used in the present invention that have been previously disclosed for use as collagen crosslinking agents include commercially available substances such as Denacol Ex-313 and Dencacol Ex-314 from Nagase Chemicals, Ltd. of Osaka, Japan (8).

In some embodiments, one or more of the crosslinkers used in the present invention are imidoesters. In some embodiments, the imidoesters are selected from the group consisting of: dimethyl adipimidate-HCl (DMA), dimethyl pimelimidate-HCl (DMP), dimethyl suberimidate-HCl (DMS), and dimethyl 3,3'-dithiobispropionimidate-HCl (DTBP). In some embodiments, one or more of the one or more crosslinkers disclosed herein are carbodiimides. In some embodiments, the carbodiimides are N,N'-dicyclohexylcarbodiimide (DCC) or N-(3-dimethylaminopropyl)-N'-ethylcarbodiimide hydrochloride (EDC). In some embodiments, the chemical compounds that are used as fixatives for cross-linking keratin and/or collagen are selected from the group consisting of: hexamethylene diisocyanate, polyepoxy compounds, N-hydroxysuccinimide esters, haloacetyls, pyridyl disulfides, hydrazides, carbonates, and aryl azides.

The above keratin crosslinking agent(s) are present in an amount of about 0.05%-10.0%6 by weight. In a preferred embodiment, the cross-linking agent(s) are present in the amount of about 0.1-2.0% by weight.

In some embodiments of the present invention, the one or more crosslinking agents are advantageously also used to lower the pH of the formulations, such as, but not limited to, polycarboxylic acids.

As disclosed above, in certain embodiments of the present invention, a plurality of crosslinking agents are used as a mixture.

Keratin Protein Fractions

In certain embodiments, the keratin protein fractions used in the inventive formulations include hydrolyzed keratin produced by alkaline and/or enzymatic hydrolysis using methods known in the art. In some embodiments, the keratin hydrolysate has a molecular weight of about 1,000-3,000. In certain embodiments, the keratin used in the inventive methods is derived from human or other mammalian sources such as goat hair, hoof or horn meals (9,10). In some embodiments, the "keratin protein fraction" is a purified form of keratin that contains predominantly, although not entirely, one distinct protein group (11). In some embodiments, the keratin protein fraction is intact intermediate filament protein capable of acting as a protective keratin layer. In some embodiments, the keratin protein fraction includes a keratin hydrolysate and a purified form of keratin. In some embodiments, the invention teaches the use of keratin hydrolysate and one or more intact intermediate filament proteins capable of acting as a protective keratin layer, or a mixture of intact intermediate filament proteins. In some embodiments, the keratin protein fraction is about 0.05%-15.0/o by weight. In some preferred embodiments, the keratin protein fraction is about 0.5-5.0% by weight. In some embodiments, small, approximately 2-100 amino acids, peptides are included in the formulation. In certain embodiments of the present invention, epigallocatechin gallate is also used in the formulation to provide additional conditioning. In some embodiments, the concentration of epigallocatechin gallate is from 0.5%-15.0% by weight. In preferred embodiments, the range is 1.0%-10.0% by weight.

Amino Acids

In some embodiments, the compositions disclosed herein include a mixture of amino acids, including, but not limited to, one or more of the 20 natural alpha-amino acids, beta- or gamma-amino acids, or any unnatural amino acids. In some embodiments, the amino acids are derived from silk fibers.

Cosmetic Ingredients

In certain embodiments, the hair-protectant, curl minimizing compositions of the present invention include curl minimizing agent in a cosmetically acceptable aqueous vehicle suitable for application at least once to human hair. In some embodiments, the hair-protectant compositions also contain conventional cosmetic hair conditioning ingredients, botanical products, and other optional cosmetic ingredients, additives, products or materials, and cosmetic adjuvants, well known in the hair care and personal care formulation arts. For heat-assisted, curl minimizing processes, the aqueous curl minimizing composition preferably contains an auxiliary hair protectant, heat-protective ingredient, such as silicone and/or a silicone derivative.

Cosmetic ingredients optionally employed in the hair-protectant compositions and systems disclosed herein are referred to by their commonly used chemical or trade names or by the international nomenclature, commonly referred to as an International Nomenclature of Cosmetic Ingredients (INCI) name, designated in any edition of the *International Cosmetic Ingredient Dictionary and Handbooks*. Numerous commercial suppliers of materials listed by INCI name, trade name, or both, can be found in any edition of the INCI Dictionary and in numerous commercial trade publications (13-14); the relevant disclosures of the INC Dictionary and each of the foregoing publications being incorporated by reference herein.

The term "cosmetic adjuvant" includes cosmetically useful product finishing and promotional additives, well known and conventionally used in the cosmetic arts to maintain the physical stability of a composition during storage (shelf-life), and the visible aesthetic appearance of a composition during storage and during the use of the composition. In some embodiments, the cosmetic adjuvants that maintain the stability of the products of the present invention include a metal-ion chelating agent, an antioxidizing agent, a preservative, an emulsifying agent, a perfume solubilizer, and the like. In some embodiments, cosmetic adjuvants of the present invention aid in enhancing the aesthetics and marketing appeal of the present invention, and include, without limitation, a product colorant, a fragrance, and the like.

Those skilled in the formulation arts can readily determine the amount of curl minimizing agent to be used in a formulation by the amount of curl minimization desired. Compositions of the various embodiments can be prepared and used in the form of aqueous liquids, or formulated as emulsions, by techniques known in the art, containing cosmetically acceptable conditioners and emulsifiers.

Surfactants

In certain embodiments, one or more surfactants are included in the hair straightening formulations of the present invention. Surfactants are surface-active agents that are able to reduce the surface tension of water and cause the product to slip across or onto the skin. Surfactants also include detergents and soap. In certain embodiments, one or more of the surfactants included in the formulations of the present invention are amphoteric. In some embodiments, one or more anionic or cationic surfactants are used. In certain embodiments, one or more of the surfactants used in the hair straightening formulations of the present invention are selected from the group consisting of: 3-aminopropane sulfonic acid, almond amide DEA, almond amidopropyl betaine, almond amidopropylamine oxide, aluminum hydrogenated tallow glutamate, aluminum lanolate, amino ethyl sulfate, aminopropyl lauryl glutamine, ammonium C12-15 alkyl sulfate, ammonium C12-15 pareth sulfate, ammonium C12-16 alkyl sulfate, ammonium C9-10 perfluoroalkylsulfonate, ammonium capryleth sulfate, ammonium capryleth-3 sulfate, ammonium cocomonoglyceride sulfate, ammonium cocosulfate, ammonium cocoyl isethionate, ammonium cocoyl sarcosinate, ammonium cumene sulfonate, ammonium dimethicone copolyol sulfate, ammonium dodecylbenzenesulfonate, ammonium isostearate, ammonium laureth sulfate, ammonium laureth-12 sulfate, ammonium laureth-5 sulfate, ammonium laureth-6 carboxylate, ammonium laureth-7 sulfate, ammonium laureth-8 carboxylate, ammonium laureth-9 sulfate, ammonium lauroyl sarcosinate, ammonium lauryl sulfate, ammonium lauryl sulfosuccinate, ammoniummyreth sulfate, ammonium myristyl sulfate, ammonium nonoxynol-30 sulfate, ammonium nonoxynol-4 sulfate, ammonium oleate, ammonium palm kernel sulfate, ammonium polyacrylate, ammonium stearate, ammonium tallate, ammonium xylene sulfonate, ammonium xylene sulfonate, amp-isostearoyl gelatinikeratin amino acids/lysine hydroxypropyltrimonium chloride, amp-isostearoyl hydrolyzed collagen, apricot kernel oil PEG-6 esters, apricot amide DEA, apricot amidopropyl betaine, arachideth-20, avocadamide DEA, avocadamidopropyl betaine, babassuamide DEA, babassuamidopropyl betaine, babassuamidopropylamine oxide, behenalkonium chloride, behenamide DEA, behenamide MEA, behenamidopropyl betaine, behenamine oxide, behentrimonium methosulfate, behenyl betaine, buteth-3 carboxylic acid, butyl polyglucose, C10-14 alkyl benzenesulfonic acid, C11-15 pareth-12, C11-15 pareth-20, C11-15 pareth-30, C11-15 pareth-40, C11-15 pareth-7 carboxylic acid, C11-15 pareth-9, C11-21-pareth-10, C12-13 pareth-10 phosphate, C12-13 pareth-5 carboxylic acid, C12-13 pareth-7, C12-15 pareth-11, C12-15 pareth-12, C12-15 pareth-2 phosphate, C12-15 pareth-7 carboxylic acid, C12-15 pareth-9, C12-15 pareth-9 hydrogenated tallowate, C14-15 pareth-13, C14-15 24 pareth-8 carboxylic acid, C22-24 pareth-33, calcium laurate, calcium myristate, canolamidopropyl betaine, caprylyl/capryl glucoside, caprylyl pyrrolidone, carboxymethyl isostearamidopropyl morpholine, cellulose acetate propionate carboxylate, ceteareth-100, ceteareth-15, ceteareth-17, ceteareth-2 phosphate, ceteareth-20, ceteareth-25, ceteareth-25 carboxylic acid, cetcareth-27, ceteareth-30, ceteareth-4 phosphate, ceteareth-40, ceteareth-5 phosphate, ceteareth-50, ceteareth-55, ceteareth-80, cetearyl polyglucose, ceteth-12, ceteth-14, ceteth-15, ceteth-16, ceteth-20, ceteth-24, ceteth-25, ceteth-45, cetethyl morpholinium ethosulfate, cetethyldimonium bromide, cetoleth-15, cetoleth-24, cetoleth-25, cetoleth-6, cetrimonium tosylate, cetyl betaine, cetyl PPG-2 isodeceth-7 carboxylate, cetylpyridmium chloride, cholesteryl/behenyl/octyldodecyl lauroyl glutamate, cocamide, cocamide DEA, cocamide MEA, cocamide MIPA, cocamidoethyl betaine, cocamidopropyl betaine, cocamidopropyl dimethyl amine, cocamidopropyl dimethylamine dihydroxymethylpropionate, cocamidopropyl dimethyl amine hydrolyzed collagen, cocamidopropyl dimethylamine lactate, cocamidopropyl dimethylamine propionate, cocamidopropyl dimethylaminohydroxypropyl hydrolyzed collagen, cocamidopropyl dimethylammonium C8-16 isoalkylsuccinyl lactoglobulin sulfonate, cocamidopropyl hydroxysultaine, cocamidopropyllauryl ether, cocamidopropylamine oxide, cocamidopropyldimonium hydroxypropyl hydrolyzed collagen, cocamine oxide, co camino butyric acid, cocaminopropionic acid, coceth-4 polyglucose, coceth-7 carboxylic acid, coc % leamidopropyl betaine, cocoamphodipropionic acid, cocobetainamido amphopropionate, cocobetaine, cocodimonium hydroxypropyl silk amino acids, coco-ethyldimonium ethosulfate, coco-glucoside, coco-hydroxysultaine, coco-morpholine oxide, coconut acid, cocopolyglucose, cocosultaine, cocotrimonium chloride, cocoyl benzyl hydroxyethyl imidazolinium chloride, cocoyl hydrolyzed collagen, cocoyl hydroxyethyl imidazoline, cocoyl sarcosinamide DEA, 25 cocoyl sarcosine, corn acid, cyclopentane carboxylic acid, DEA-C12-15 alkyl sulfate, DEA-cetyl phosphate, DEA-cetyl sulfate, DEA-cocoamphodipropionate, DEA-cyclocarboxypropylolcate, DEA-dodecy lbenzenesulfonate, DEA-iso stearate, DEA-Laureth sulfate, DEA-lauryl sulfate, DEA-methyl myristate sulfonate, DEA-myreth sulfate, DEA-myristate, DEA-myristyl sulfate, DEA-oleth-10 phosphate, DEA-oleth-20 phosphate, DEA-oleth-3 phosphate, DEA-oleth-5 phosphate, deceth-4 phosphate, deceth-7 carboxylic acid, decyl betaine, decyl glucoside, decyl polyglucose, decylamine oxide, diammonium dimethicone copolyol sulfosuccinate, diammonium lauramido-MEA sulfosuccinate, diammonium lauryl sulfosuccinate, diammonium oleamido PEG-2 sulfosuccinate, diamyl sodium sulfosuccinate, dicapryl sodium sulfosuccinate, dicetyldimonium chloride, dicocodimonium chloride, dicyclohexyl sodium sulfosuccinate, didecyldimonium chloride, diethanolaminooleamide DEA, diethylamine laureth sulfate, diethylaminoethyl cocoate, diethylaminoethyl PEG-5 cocoate, diethylaminoethyl stearate, diheptyl sodium sulfosuccinate, dihexyl sodium sulfosuccinate, dihydrogenated C16-18 amido benzoic acid, dihydrogenated tallow benzylmonium chloride, dihydrogenated tallow methylamine, dihydrogenated tallow phthalate, dihydroxyethyl C12-15 alkoxypropylamine oxide, dihydroxyethyl C8-10 alkoxypropylamine oxide, dihydroxyethyl C9-11 alkoxypropylamine oxide, dihydroxyethyl cocamine oxide, dihydroxyethyl lauramine oxide, dihydroxyethyl soya glycinate, dihydroxyethyl stearamine oxide, dihydroxyethyl tallow glycinate, dihydroxyethyl tallowamine HCl, dihydroxyethyl tallowamine oleate, dihydroxyethyl tallowamine oxide, diisobutyl sodium sulfosuccinate, dilaureth-10 phosphate, dilaureth-4 dimonium chloride, dilauryldimonium chloride, dilinoleamidopropyl dimethylamine dimethicone copolyol phosphate, dimethicone propyl PG-betaine, dimethyl cocamine, dinonoxynol-9 citrate, dioctyl sodium sulfosuccinate, dioctyldodeceth-2 lauroyl glutamate, dioctyldodecyl-lauroyl 26 glutamate, dioleth-8 phosphate, dipropylene glycol salicylate, disodium bisethylphenyl triaminotriazine stilbenedisulfonate, disodium C12-15 pareth sulfosuccinate, disodium caproamphodiacetate, disodium caproamphodipropionate, disodium capryloamphodiacetate, disodium capryloamphodipropionate, disodium cetearyl sulfosuccinate, disodium cocamido MEAsulfosuccinate, disodium cocamido MIPA-sulfosuccinate, disodium cocamido PEG-3 sulfosuccinate, disodium cocaminopropyl iminodiacetate, disodium cocoamphocarboxyethy lhydroxypropy lsulfonate, disodium cocoamphodiacetate, disodium cocoamphodipropionate, disodium cocopolyglucose citrate, disodium cocopolyglucose sulfosuccinate, disodium cocoyl butyl gluceth-10 sulfosuccinate, disodium cocoyl glutamate, disodium deceth-5 sulfosuccinate, disodium deceth-6 sulfosuccinate, disodium dicarboxyethyl cocopropylenediamine, disodium dihydroxyethyl sulfosuccinylundecylenate, disodium dimethicone copolyol sulfosuccinate, disodium distyrylbiphenyl disulfonate, disodium hydrogenated cottonseed glyceride sulfosuccinate, disodium hydrogenated tallow glutamate, disodium hydroxydecyl sorbitol citrate, disodium isodecyl sulfosuccinate, disodium isostcaramido MEA-sulfosuccinatc, disodium isostcaramido MIPA-sulfosuccinate, disodium isostearoamphodiacetate, disodium isostearoamphodipropionate, disodium isostearylsulfosuccinate, disodium laneth-5 sulfosuccinate, disodium lauramido MEA-sulfosuccinate, disodium lauramido PEG-2 sulfosuccinate, disodium lauramido PEG-5 sulfosuccinate, disodium laureth sulfosuccinate, disodium laureth-12 sulfosuccinate, disodium laureth-5 carboxyamphodiacetate, disodium laureth-6 sulfosuccinate, disodium laureth-7 citrate, disodium laureth-9 sulfosuccinate, disodium lauriminodipropionate, disodium lauroamphodiacetate, disodium lauroamphodipropionate, disodium lauryl sulfosuccinate, disodium myristamido MEA-sulfosuccinate, disodium nonoxynol-10 sulfosuccinate, disodium oleamido MEA-sulfosuccinate, disodium oleamido 27 MIPA-sulfosuccinate, disodium oleamido PEG-2 sulfosuccinate, disodium oleoamphodipropionate, disodium oleth-3 sulfosuccinate, disodium oleyl sulfosuccinate, disodium palmitamido PEG-2 sulfosuccinate, disodium palmitoleamido PEG-2 sulfosuccinate, disodium PEG-10 laurylcitrate sulfosuccinate, disodium PEG-4 cocamido MIPA-sulfosuccinate, disodium PEG-8 glyceryl caprylate/caprate, disodium PEG-8 ricinosuccinate, disodium PPG-2-isodeceth-7 carboxyamphodiacetate, disodium ricinolcamido MEA-sulfosuccinate, disodium sitostereth-14 sulfosuccinate, disodium stearamido MEA-sulfosuccinate, disodium steariminodipropionate, disodium stearoamphodiacetate, disodium stearyl sulfosuccinamate, disodium stearyl sulfosuccinate, disodium succinate, disodium succinoyl glycyrrhetinate, disodium tallamido MEA-sulfosuccinate, disodium tallow sulfosuccinamate, disodium tallow amido MEAsulfosuccinate, disodium tallow amphodiacetate, disodium tallow iminodipropionate, disodium tetrapropenyl succinate, disodium tridecylsulfosuccinate, disodium undecylenamido MEA-sulfosuccinate, disodium undecylenamido PEG-2 sulfosuccinate, disodium wheat germamido MEA-sulfosuccinate, disodium wheat germamido PEG-2 sulfosuccinate, disodium wheat germ amphodiacetate, disoyadimonium chloride, disteareth-2 lauroyl glutamate, disteareth-5 lauroyl glutamate, disteareth-6 dimonium chloride, ditallowamidoethyl hydroxypropylamine, ditallowedimonium chloride, di-TEA-olcamido PEG-2 sulfosuccinate, di-TEA-palmitoyl aspartate, ditridecyl sodium sulfosuccinate, dodecylbenzene sulfonic acid, dodecylbenzyltrimonium chloride, dodecylxylyldimonium chloride, dodoxynol-12, dodoxynol-5 dodoxynol-6, dodoxynol-7, dodoxynol-9, erucamidopropyl hydroxysultaine, ethyl butylacetylaminopropionate, ethyl guiazulene sulfonate, ethyl PEG-15 cocamine sulfate, glycol stearate, hexeth-4 carboxylic acid, hydrogenated castor oil, hydrogenated coconut acid, hydrogenated ditallowamine, hydrogenated menhaden acid, hydrogenated tallow amide, 28 hydrogenated tallow betaine, hydrogenated tallowamide DEA, hydrogenated tallowamine, hydrogenated tallowamine oxide, hydrogenated tallowtrimonium chloride, hydrolyzed beeswax, hydroxyceteth-60, hydroxyethyl carboxymethyl cocamidopropylamine, hydroxyethyl cetyldimonium chloride, hydroxyethyl cetyldimonium phosphate, hydroxyethyl hydroxypropyl C12-15 alkoxypropylamine oxide, hydroxyethylbutylamino laureth sulfate, isoceteth-30, isopropanolamine lanolate, isopropyl hydroxycetyl ether, isopropylamine dodecylbenzenesulfonate, isostearamidomorpholine stearate, isostearamidopropyl betaine, isostearamidopropyl morpholine oxide, isostearamidopropylamine oxide, isosteareth-11 carboxylic acid, isosteareth-50, isosteareth-6 carboxylic acid, isostearic acid, isostearoyl hydrolyzed collagen, laneth-40, laneth-50, laneth-75, lanolinamide DEA, lauramide/myristamide DEA, lauramidopropyl betaine, lauramidopropylamine oxide, lauramine oxide, laureth-1, laureth-10, laureth-10 carboxylic acid, laureth-11 carboxylic acid, laureth-13 carboxylic acid, laureth-14 carboxylic acid, laureth-17 carboxylic acid, laureth-2, laureth-20, laureth-23, laureth-25, laureth-3, laureth-3 carboxylic acid, laureth-3 phosphate, laureth-30, laureth-4, laureth-4 carboxylic acid, laureth-40, laureth-5, laureth-5 carboxylic acid, laureth-6, laureth-6 carboxylic acid, laureth-6 citrate, laureth-7, laureth-7 citrate, laureth-7 tartrate, laureth-8 phosphate, lauroamphodipropionic acid, lauroyl hydrolyzed collagen, lauroyl sarcosine, lauryl betaine, lauryl hydroxysultaine, lauryl isoquinolinium bromide, lauryl polyglucose, lauryl pyrrolidone, lauryl sultaine, laurylpyridinium chloride, lysine thiazolidine carboxylate, magnesium cocoate, magnesium coco-sulfate, magnesium lanolate, magnesium laureth sulfate, magnesium laureth-1 carboxylate, magnesium laureth-16 sulfate, magnesium laureth-5 sulfate, magnesium laureth-8 sulfate, magnesium lauryl hydroxypropyl sulfonate, magnesium lauryl sulfate, magnesium myreth sulfate, magnesium oleth sulfate, magnesium PEG-3 cocamide 29 sulfate, magnesium tallowate, mannitan oleate, MEA-dicetearyl phosphate, MEA-laureth sulfate, MEA-laureth-6 carboxylate, MEA-lauryl sulfate, MEA-PPG-6-laureth-7-carboxylate, meroxapol105, meroxapol 108, meroxapol 171, meroxapol 172, meroxapol 174, meroxapol 178, meroxapol 251, meroxapol 252, meroxapol 254, meroxapol255, meroxapol258, meroxapol311, meroxapol312, meroxapol314, methoxy-PEG-7 rutinyl succinate, methyl morpho line oxide, methylpyrrolidone, methylbenzethonium chloride, minkamide DEA, minkamidopropyl betaine, minkamidopropyl dimethylamine, minkamidopropylamine oxide, MIPA C12-15 pareth sulfate, MIPA-dodecylbenzenesulfonate, MIPA-laureth sulfate, MIPA-lauryl sulfate, mixed isopropanolamines lanolate, mixed isopropanolamines lauryl sulfate, mixed isopropanolamines myristate, myreth-2 myristate, myreth-3 carboxylic acid, myreth-3 myristate, myreth-5 carboxylic acid, myristamidopropyl betaine, myristamidopropyl dimethyl amine dimethicone copolyol phosphate, myristamidopropyl dimethylamine phosphate, myristamidopropylamine oxide, myristamine oxide, myristaminopropionic acid, myristoyl hydrolyzed collagen, myristoyl sarcosine, myristylicetyl amine oxide, myristyl betaine, noneth-8, nonoxynol-10 carboxylic acid, nonoxynol-10 phosphate, nonoxynol-100, nonoxynol-11, nonoxynol-12, nonoxynol-13, nonoxynol-14, nonoxynol-15, nonoxynol-18, nonoxynol-2, nonoxynol-20, nonoxynol-23, nonoxynol-30, nonoxynol-4, nonoxynol-40, nonoxynol-44, nonoxynol-5, nonoxynol-5 carboxylic acid, nonoxynol-50, nonoxynol-6, nonoxynol-6 phosphate, nonoxynol-7, nonoxynol-8, nonoxynol-8 carboxylic acid, nonoxynol-9, nonoxynol-9 phosphate, nonyl nonoxynol-10, nonyl nonoxynol-10 phosphate, nonyl nonoxynol-100, nonyl nonoxynol-15 phosphate, nonyl nonoxynol-150, nonyl nonoxynol-24 phosphate, nonyl nonoxynol-49, nonyl nonoxynol-7 phosphate, nonyl nonoxynol-9 phosphate, octeth-3 carboxylic acid, octoxynol-1, octoxynol-10, octoxynol-11, octoxynol-13, octoxynol-16, octoxynol-20 carboxylic acid, octoxynol-3, 30 octoxynol-30, octoxynol-40, octoxynol-5, octoxynol-7, octoxynol-70, octoxynol-8, octoxynol-9, octoxynol-9 carboxylic acid, oleamidopropyl betaine, oleamidopropyl hydroxysultaine, oleamidopropylamine oxide, oleamine oxide, oleoyl hydrolyzed collagen, oleoyl sarcosine, oleth-10, oleth-10 carboxylic acid, oleth-10 phosphate, oleth-12, oleth-15, oleth-16, oleth-2, oleth-20, oleth-20 phosphate, oleth-23, oleth-25, oleth-3 carboxylic acid, oleth-3 phosphate, oleth-4 phosphate, oleth-44, oleth-5 phosphate, oleth-50, oleth-6 carboxylic acid, oleyl betaine, olivamide DEA, olivamidopropyl betaine, olivamidopropylamine oxide, olive oil PEG-10 esters, palm kemelamide DEA, palm kemelamide MEA, palm kemelamide MIPA, palm kemelamidopropyl betaine, palmamide DEA, palmamide MEA, palmamide MIPA, palmamidopropyl betaine, palmitamidopropyl betaine, palmitamidopropylamine oxide, palmitamine oxide, palmitoyl hydrolyzed collagen, palmitoyl hydrolyzed wheat protein, pea ethyl cocoyl arginate, peanutamide MEA, peanutamide MIPA, PEG/PPG-300/55 copolymer, PEG-10 castor oil, PEG-10 cocamine, PEG-10 coco-benzonium chloride, PEG-10 isostearate, PEG-10 soyamine, PEG-10 stearate, PEG-10 stearyl benzonium chloride, PEG-100 castor oil, PEG-100 hydrogenated castor oil, PEG-100 lanolin, PEG-100 stearate, PEG-II cocamide, PEG-120 glyceryl stearate, PEG-120 stearate, PEG-15 castor oil, PEG-15 cocamine, PEG-15 cocomonium chloride, PEG-15 hydrogenated tallow amine, PEG-15 oleammonium chloride, PEG-15 soyamine, PEG-15 stearmonium chloride, PEG-150 distearate, PEG-150 laurate, PEG-150 oleate, PEG-150 stearate, PEG-16 hydrogenated castor oil, PEG-175 distearate, PEG-2 castor oil, PEG-2 coco-benzonium chloride, PEG-2 cocomonium chloride, PEG-2 hydrogenated tallow amine, PEG-2 oleammonium chloride, PEG-2 sorbitan isostearate, PEG-2 soyamine, PEG-2 stearamide carboxylic acid, PEG-20 castor oil, PEG-20 cocamine, PEG-20 glyceryl isostearate, PEG-20 hydrogenated castor oil, PEG-20 hydrogenated tallow amine, PEG-20 31 laurate, PEG-20 myristate, PEG-20 oleate, PEG-20 palmitate, PEG-20 sorbitan beeswax, PEG-20 sorbitan isostearate, PEG-20 stearate, PEG-20 tallate, PEG-200 castor oil, PEG-200 glyceryl stearate, PEG-200 glyceryl tallowate, PEG-200 hydrogenated castor oil, PEG-200 trihydroxystearin, PEG-23 oleate, PEG-25 castor oil, PEG-25 diethylmonium chloride, PEG-25 glyceryl stearate, PEG-25 hydrogenated castor oil, PEG-28 glyceryl tallowate, PEG-29 castor oil, PEG-3 castor oil, PEG-3 cocamide, PEG-3 lauramine oxide, PEG-3 oleamide, PEG-30 castor oil, PEG-30 glyceryl cocoate, PEG-30 glyceryl isostearate, PEG-30 glyceryl oleate, PEG-30 glyceryl stearate, PEG-30 hydrogenated castor oil, PEG-30 hydrogenated tallow amine, PEG-30 oleamine, PEG-30 stearate, PEG-32 laurate, PEG-32 oleate, PEG-32 stearate, PEG-33 castor oil, PEG-35 castor oil, PEG-35 hydrogenated castor oil, PEG-35 stearate, PEG-36 castor oil, PEG-36 oleate, PEG-36 stearate, PEG-4 castor oil, PEG-4 laurate, PEG-4 stearamide, PEG-40 castor oil, PEG-40 hydrogenated castor oil, PEG-40 hydrogenated tallow amine, PEG-40 sorbitan diisostearate, PEG-40 sorbitan peri so stearate, PEG-40 sorbitan peroleate, PEG-40 sorbitan stearate, PEG-40 sorbitol hexaoleate, PEG-40 stearate, PEG-44 sorbitan laurate, PEG-45 hydrogenated castor oil, PEG-45 stearate, PEG-45 stearate phosphate, PEG-4-PPG-7 C13/C15 alcohol, PEG-5 castor oil, PEG-5 cocamide, PEG-5 ditridecylmonium chloride, PEG-5 glyceryl stearate, PEG-5 hydrogenated castor oil, PEG-5 hydrogenated com glycerides, PEG-5 soyamine, PEG-5 stearate, PEG-5 stearyl ammonium chloride, PEG-5 stearyl ammonium lactate, PEG-5 tallow benzonium chloride, PEG-50 castor oil, PEG-50 hydrogenated castor oil, PEG-50 stearamine, PEG-50 stearate, PEG-6 cocamide, PEG-6 oleate, PEG-6 palmitate, PEG-6 sorbitan beeswax, PEG-60 castor oil, PEG-60 glyceryl isostearate, PEG-60 hydrogenated castor oil, PEG-60 sorbitan stearate, PEG-66 trihydroxystearin, PEG-7 cocamide, PEG-7 glyceryl cocoate, PEG-7 hydrogenated castor oil, PEG-7 oleate, PEG-75 castor oil, PEG-75 dioleate, PEG-75 lanolin, 32 PEG-75 lanolin oil, PEG-75 lanolin wax, PEG-75 laurate, PEG-75 oleate, PEG-75 sorbitan laurate, PEG-75 stearate, PEG-78 glyceryl cocoate, PEG-8 castor oil, PEG-8 laurate, PEG-8 propylene glycol cocoate, PEG-8 ricinoleate, PEG-8 sorbitan beeswax, PEG-8 soyamine, PEG-8 stearate, PEG-80 glyceryl cocoate, PEG-80 hydrogenated castor oil, PEG-80 jojoba acid, PEG-80 jojoba alcohol, PEG-80 sorbitan laurate, PEG-80 sorbitan palmitate, PEG-85 lanolin, PEG-9 castor oil, PEG-9 ricinoleate, PEG-90 stearate, pentaerythrityl tetraisostearate, poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, poloxamer 407, polyglyceryl-4-PEG-2 cocamide, polysorbate 20, polysorbate 40, polysorbate 60, polysorbate 65, polysorbate 80, polysorbate 85, potassium abietoyl hydrolyzed collagen, potassium C9-15 alkyl phosphate, potassium castorate, potassium cetyl phosphate, potassium cocoate, potassium cocoyl glutamate, potassium cocoyl hydrolyzed collagen, potassium cornate, potassium cyclocarboxypropyloleate, potassium dihydroxyethyl cocamine oxide phosphate, potassium dodecylbenzenesulfonate, potassium laurate, potassium lauroyl collagen amino acids, potassium lauroyl hydrolyzed collagen, potassium lauroyl hydrolyzed soy protein, potassium lauryl hydroxypropyl sulfonate, potassium lauryl sulfate, potassium methyl cocoyl taurate, potassium myristate, potassium myristoyl hydrolyzed collagen, potassium octoxynol-12 phosphate, potassium oleate, potassium oleoyl hydrolyzed collagen, potassium olivate, potassium palmitate, potassium ricinoleate, potassium stearate, potassium stearoyl hydrolyzed collagen, potassium tallowate, potassium toluenesulfonate, potassium undecylenoyl hydrolyzed 33 collagen, potassium xylene sulfonate, PPG-IO cetyl ether, PPG-IO cetyl ether phosphate, PPG-15-PEG-II hydrogenated lauryl alcohol ether, PPG-17 butyl ether, PPG-20 butyl ether, PPG-24 butyl ether, PPG-25 diethylmonium chloride, PPG-3 hydrogenated castor oil, PPG-30-buteth-30, PPG-4 laureth-5, PPG-40 diethylmonium chloride, PPG-50 cetyl ether, PPG-5-ceteth-10 phosphate, PPG-5-ceteth-20, PPG-8-ceteth-IO, PPG-8-ceteth-20, PPG-9 diethylmonium chloride, propylene glycol soyate, quaternium-14, quaternium-18, quaternium-24, quaternium-52, raffinose oleate, rapeseedamidopropyl benzyldimonium chloride, ricinoleamidopropyl betaine, ricinoleth-40, saponins, sesamide DEA, sesamidopropyl betaine, sesamidopropyl dimethylamine, sesamidopropylamine oxide, sodium/MEA laureth-2 sulfosuccinate, sodium/TEA-lauroyl collagen amino acids, sodium/TEAlauroyl hydrolyzed collagen, sodiumlTEA-lauroyl hydrolyzed keratin, sodiumlTEA-lauroyl keratin amino acids, sodium/TEA-undecylenoyl collagen amino acids, sodium/TEA-undecylenoyl hydrolyzed collagen, sodium behenoyl lactylate, sodium bisglycol ricinosulfosuccamate, sodium butoxynol-12 sulfate, sodium C11-15 pareth-7 carboxylate, sodium C12-13 pareth sulfate, sodium C12-14 olefin sulfonate, sodium C12-15 alkoxypropyl iminodipropionate, sodium C12-15 alkyl sulfate, sodium C12-15 pareth sulfate, sodium C12-15 pareth-15 sulfonate, sodium C12-15 pareth-3 sulfonate, sodium C12-15 pareth-6 carboxylate, sodium C12-15 pareth-7 carboxylate, sodium C12-15 pareth-7 sulfonate, sodium C12-18 alkyl sulfate, sodium C13-17 alkane sulfonate, sodium C14-16 olefin sulfonate, sodium C14-17 alkyl sec sulfonate, sodium C14-18 olefin sulfonate, sodium C16-18 olefin sulfonate, sodium C16-20 alkyl sulfate, sodium C8-16 isoalkylsuccinyl lactoglobulin sulfonate, sodium C9-22 alkyl sec sulfonate, sodium caproamphoacetate, sodium caproamphohydroxypropylsulfonate, sodium caproamphopropionate, sodium caprylate, sodium capryleth-2 carboxylate, sodium capryleth-9 34 carboxylate, sodium caproamphoacetate, sodium capryloamphohydroxypropylsulfonate, sodium capryloamphopropionate, sodium caprylyl sulfonate, sodium carboxyethyl tallow polypropylamine, sodium carboxymethyl cocopolypropylamine, sodium carboxymethyl oleyl polypropylamine, sodium carboxymethyl tallow polypropylamine, sodium castorate, sodium cetearyl sulfate, sodium ceteth-13 carboxylate, sodium cetyl sulfate, sodium cocaminopropionate, sodium coceth sulfate, sodium coco/hydrogenated tallow sulfate, sodium cocoamphoacetate, sodium cocoamphohydruxypropylsulfonate, sodiumcocoamphopropionate, sodium cocoate, sodium cocoglyceryl ether sulfonate, sodium cocomonoglyceride sulfate, sodium cocomonoglyceride sulfonate, sodium cocopolyglucose tartrate, sodium coco-sulfate, sodium cocoyl collagen amino acids, sodium cocoyl glutamate, sodium cocoyl hydrolyzed collagen, sodium cocoyl hydrolyzed keratin, sodium cocoyl hydrolyzed rice protein, sodium cocoyl hydrolyzed soy protein, sodium cocoyl hydrolyzed wheat protein, sodium cocoyl isethionate, sodium cocoyllactylate, sodium cocoyl sarcosinate, sodium comamphopropionate, sodium cumenesulfonate, sodium cyclopentane carboxylate, sodium deceth sulfate, sodium deceth-2 carboxylate, sodium decylbenzenesulfonate, sodium dicarboxyethylcoco phosphoethyl imidazoline, sodium diethylaminopropyl cocoaspartamide, sodium dihydroxycetyl phosphate, sodium dilaureth-7 citrate, sodium dodecylbenzenesulfonate, sodium ethyl 2-sulfolaurate, sodium glycereth-I polyphosphate, sodium glyceryl oleate phosphate, sodium guiazulene sulfonate, sodium hydrogenated tallow glutamate, sodium isostearoamphoacetate, sodium isostearoamphopropionate, sodium laneth sulfate, sodium lauramido diacetate, sodium lauramidopropyl hydroxyphostaine, sodium lauraminopropionate, sodium laurate, sodium laureth sulfate, sodium laureth-11 carboxylate, sodium laureth-12 sulfate, sodium laureth-13 carboxylate, sodium laureth-14 carboxylate, sodium laureth-17 carboxylate, sodium laureth-4 35 carboxylate, sodium laureth-4 phosphate, sodium laureth-5 carboxylate, sodium laureth-5 sulfate, sodium laureth-6 carboxylate, sodium laureth-7 sulfate, sodium laureth-7 tartrate, sodium laureth-8 sulfate, sodium lauriminodipropionate, sodium lauroampho PG-acetate phosphate, sodium lauroamphoacetate, sodium lauroamphohydroxypropylsulfonate, sodium lauroyl aspartate, sodium lauroyl glutamate, sodium lauroyl hydrolyzed collagen, sodium lauroyl isethionate, sodium lauroyl methylaminopropionate, sodium lauroyl sarcosinate, sodium lauroyl taurate, sodium lauryl phosphate, sodium lauryl sulfate, sodium lauryl sulfoacetate, sodium lignosulfonate, sodium methyl-2-sulfolaurate, sodium methyl cocoyl taurate, sodium methyl lauroyl taurate, sodium methyl myristoyl taurate, sodium methyl oleoyl taurate, sodium methyl palmitoyl taurate, sodium methyl stearoyl taurate, sodiummethylnaphthalenesulfonate, sodium myreth sulfate, sodium myristate, sodium myristoamphoacetate, sodium myristoyl glutamate, sodium myristoyl isethionate, sodium myristoyl sarcosinate, sodium myristyl sulfate, sodium nonoxynol-1 sulfate, sodium nonoxynol-10 sulfate, sodium nonoxynol-4 sulfate, sodium nonoxynol-6 phosphate, sodium nonoxynol-9 phosphate, sodium octoxynol-2 ethane sulfonate, sodium octyl sulfate, sodium oleate, sodium oleoamphoacetate, sodium oleoamphohydroxypropylsulfonate, sodium oleoamphopropionate, sodium oleoyl isethionate, sodium oleth-7 phosphate, sodium oleth-8 phosphate, sodium olivate, sodium palm kernelate, sodium palmate, sodium palmitate, sodium PEG-6 cocamide carboxylate, sodium polydimethylglycinophenolsulfonate, sodium polynaphthalenesulfonate, sodium polystyrene sulfonate, sodium ricinoleoamphoacetate, sodium shale oil sulfonate, sodium soya hydrolyzed collagen, sodium stearate, sodium stearoamphoacetate, sodium stearoamphopropionate, sodium stearyl betaine, sodium stearyl sulfate, sodium tallamphopropionate, sodium tallow sulfate, sodium tallowamphoacetate, sodium tallowate, sodium toluenesulfonate, sodium trideceth 36 sulfate, sodium trideceth-12 carboxylate, sodium trideceth-3 carboxylate, sodium trideceth-6 carboxylate, sodium trideceth-7 carboxylate, sodium trideceth-8 carboxylate, sodium tridecyl sulfate, sodium tridecylbenzenesulfonate, sodium trilaureth-4 phosphate, sodium undecy lenoamphoacetate, sodium undecy lenoamphopropionate, sodium wheat germamphoacetate, sodium xylenesulfonate, soya hydroxyethyl imidazoline, soyamide DEA, soyamidopropyl betaine, soyamidopropyl dimethylamine, soyamidopropyl ethyldimonium ethosulfate, soytrimonium chloride, stearamidopropyl betaine, stearamidopropyl dimethyl amine, stearamidopropylamine oxide, stearamine oxide, steareth-10, steareth-100, steareth-2, steareth-20, steareth-21, steareth-2S, steareth-27, steareth-30, steareth-40, steareth-50, stearoyl sarcosine, stearyl betaine, sucrose laurate, sucrose palmitate, sulfated castor oil, sulfated glyceryl oleate, sulfated olive oil, sulfated peanut oil, sulfonated castor oil, tallow amide, tallow amine, tallow betaine, tallow dihydroxyethyl betaine, tallow hydroxy ethyl imidazoline, tallowamidopropyl betaine, tallowamidopropyl dimethylamine, tallowamidopropyl hydroxysultaine, tallowamidopropylamine oxide, tallowamine oxide, tallowedimonium propyltrimonium dichloride, tallowtrimonium chloride, TEA-abietoyl hydrolyzed collagen, TEA-C10-12 alkyl sulfate, TEA-C10-14 alkyl benzenesulfonate, TEA-C10-15 alkyl sulfate, TEA-C12-15 alkyl sulfate, TEA-cocoate, TEA-cocosulfate, TEA-cocoyl glutamate, TEA-cocoyl hydrolyzed collagen, TEA-cocoyl sarcosinate, TEA-dodecylbenzenesulfonate, TEAhydrogenated tallow glutamate, TEA-isostearate, TEA-isostearoyl hydrolyzed collagen, TEAlauraminopropionate, TEA-laureth sulfate, TEA-lauroyl collagen amino acids, TEA-lauroyl glutamate, TEA-lauroyl hydrolyzed collagen, TEA-lauroyl keratin amino acids, TEA-lauroyl lactylate, TEA-lauroyl sarcosinate, TEA-lauryl sulfate, TEA-myristaminopropionate, TEAmyristate, TEA-myristoyl hydrolyzed collagen, TEA-oleate, TEA-oleoyl hydrolyzed collagen, 37 TEA-oleoyl sarcosinate, TEA-oleyl sulfate, TEA-palm kernel sarcosinate, TEA-palmitate, TEAPEG-3 cocamide sulfate, TEA-stearate, TEA-tallate, TEA-tridecylbenzenesulfonate, TEAundecylenoyl hydrolyzed collagen, tetrasodium dicarboxyethyl stearyl sulfosuccinamate, TIPA-laureth sulfate, TIPA-lauryl sulfate, TIPA-stearate, tocophereth-10, tocophereth-12, tocophereth-18, tocophereth-5, tocophereth-50, toluene sulfonic acid, triceteareth-4 phosphate, triceteth-5 phosphate, trideceth-12, trideceth-15 carboxylic acid, trideceth-19 carboxylic acid, trideceth-3 carboxylic acid, trideceth-4 carboxylic acid, trideceth-6, trideceth-6 phosphate, trideceth-7 carboxylic acid, trideceth-8, tridecylbenzenesulfonic acid, triheptanoin, trilauryl phosphate, triolein PEG-6 esters, trisodium lauroampho PG-acetate phosphate chloride, tristearyl phosphate, undecyl polyglucose, undecylenamidopropyl betaine, undecylenamidopropylamine oxide, undecylenoyl wheat amino acids, wheat germamide DEA, wheat germamidopropyl betaine, wheat germamidopropyl dimethylamine, wheat germamidopropyl dimethyl amine lactate, wheat germamidopropylamine oxide, xylene sulfonic acid, zinc pentadecene tricarboxylate, and combinations thereof. In some embodiments, the surfactants are present in an amount of about 0.1%-15.0% by weight. In some embodiments, the preferred range is about 1.0%-10.0% by weight.

Emollients

In certain embodiments, the hair straightening formulations include one or more emollients. As defined herein, an "emollient" is a material that protects against wetness or irritation, softens, soothes, supples, coats, lubricates, moisturizes, protects, and/or cleanses the skin. In certain embodiments, one or more of the emollients included in the hair straightening formulations disclosed herein is a silicone compound. In certain embodiments, the silicone compound is selected from the group consisting of: dimethicone, cyclomethicone, dimethicone copolyol, a mixture of cyclopentasiloxane and cyclopentasiloxane polysilicone. In certain embodiments, the inventive formulations disclosed herein include polyols. In some embodiments, the polyols are selected from the group consisting of: sorbitol, glycerin, propylene glycol, ethylene glycol, polyethylene glycol, caprylyl glycol, polypropylene glycol, 1,3-butane diol, hexylene glycol, isoprene glycol, xylitol. In some embodiments, the present invention discloses the use of ethylhexyl palmitate, a triglyceride such as caprylic/capric triglyceride, and fatty acid ester such as cetearyl isononanoate or cetyl palmitate as emollients. In certain embodiments, the emollient is selected from the group consisting of: dimethicone, amidodimethicone, dimethiconol, cyclopentasiloxane, potassium dimethicone PEG-7 panthenyl phosphate, cetearyl isononanoate, cetyl palmitate, and combinations thereof. In some embodiments, the emollient is about 0.5-15.0% by weight of the hair straightening formulations. In certain preferred embodiments, the emollient is about 1.0-10.0% by weight of the hair straightening formulations.

Emulsifiers

In certain embodiments, formulations of the present invention include one or more emulsifiers. Emulsifiers used in the hair straightening formulations of the present invention include a copolymer of an unsaturated ester and styrene sulphonate monomer, cetearyl alcohol, glyceryl ester, polyoxyethylene glycol ether of cetearyl alcohol, stearic acid, polysorbate-20, ceteareth-20, lecithin, glycol stearate, polysorbate-60 and/or polysorbate-80. In some embodiments, the emulsifier is about 0.05-15.0% by weight of the hair straightening formulations disclosed herein. In preferred embodiments, the emulsifier is about 0.1-10.0% by weight of the hair straightening formulations disclosed herein.

Preservatives

In some embodiments, one or more preservatives are included in the hair straightening formulations disclosed herein. In some embodiments, one or more of the preservatives includes one or more glycerin containing compounds. In some embodiments the preservatives include a chemical selected from the group consisting of: glycerin, ethylhexylglycerin, and phenoxyethanol. In some embodiments, the preservatives further include benzyl alcohol, EDTA, and/or potassium sorbate. In some embodiments, the preservatives of the formulations disclosed herein include plant-derived compounds or compound mixtures. In certain embodiments, the plant-derived compounds or compound mixtures are selected from the group consisting of: grapefruit seed extract, radish root ferment filtrate, *Aloe barbadensis* leaf ferment filtrate, *Sorbus aucuparia* fruit ferment filtrate, *Ribes nigrum* (black currant) fruit extract, *Sambucus nigra* fruit extract, *japonica* root extract, *Zingiber officinale* (ginger) root extract, *Allium sativum* (garlic) bulb extract, *Origanum vulgare* leaf extract, *Thymus vulgaris* (thyme) leaf extract, *Rosmarinus officinalis* (rosemary) leaf extract, and combinations thereof. In preferred embodiments, the hair straightening formulations are paraben-free. In certain embodiments, the preservative component is from about 0.05-15% by weight of the hair straightening formulations disclosed herein. In preferred embodiments, the preservative component is from about 0.1-5.0% by weight of the hair straightening formulations disclosed herein.

Skin Protecting Agents

In certain embodiments, the hair straightening formulations disclosed herein include one or more skin protecting agents. In some embodiments, the skin protecting agents include one or more agents that prevent the transmission of microbes. In some embodiments, the hair straightening formulations disclosed herein include antibacterial agents. In some embodiments, the skin protecting agents include skin cleansing agents. In certain embodiments, the skin cleansing agents include one or more disinfectants and/or antiseptic agents. In some embodiments, the skin protecting agents include ultraviolet to visible radiation blocking agents. In some embodiments, skin protecting agents included in the hair straightening formulations of the present invention include cleansing agents. In some embodiments, the cleansing agents are selected from the group consisting of: sodium cocyl amino acids, benzalkonium chloride, centrimonium chloride, and combinations thereof. In some embodiments, the skin protecting component is about 0.1-10.0% by weight of the hair straightening formulations disclosed herein. In some preferred embodiments, the skin protecting component is about 0.5-5.0% by weight of the formulations disclosed herein.

Botanicals

In certain embodiments, the hair straightening formulations disclosed herein include one or more botanical, or botanical-derived ingredients. In some embodiments, one or more botanicals are derived from the group consisting of: Castanha do Brasil (Brazil nut, *Bertholletia excelsa*) oil and butter, *Mauritia* fruit, essential Buriti fruit oil (*Mauritia flexuosa*), Andiroba seed oil, Mango seed oil and butter, Jojoba oil, Olive squalane, oil, and leaf extract. Sunflower oil, Sangre de Drago, Samambaia, Una de Gato, Camu Camu, Cupuacu oil and butter, Espinheira Santa, Maracuja (passion flower) oil, Vitamin E, Sandelwood essential oil, avocado oil, coconut (*Cocos nucifera*) oil, sweet almond oil. *Aloe* Vera (*Aloe Barbadensis*) leaf juice, butter, and oil, Shea butter, Macadamia nut oil, Blueberry seed oil, Pomegranate seed oil, Green tea extract, Lemon essential oil, Lime essential oil, Mandarin oil and butter, Tangerine oil and butter, Orange blossom, sweet Orange oil, Orange wild oil, Orange essence oil, Vanilla extract, Guarana extract. Palm butter, and Wheat proteins. One of skill in the art would readily appreciate that additional botanicals could be used in addition to those disclosed herein.

Diluents

The term "diluent," as used herein refers to substances that may be used to dilute the active ingredient, as disclosed above. In some embodiments, water is used as the diluent. In some embodiments, the formulations require use of greater than 1.0% water to be effective. Advantageously, greater than 5.0% water is used. Preferably, greater than 50% water is used. Even more preferably, greater than 70% water is used. In certain embodiments, alcohols are used. In some embodiments, the alcohols are used at low concentrations to enhance shaft penetration and/or reduce odor. In some embodiments the concentration of the alcohols used is about 0.5%. In some embodiments, the alcohols used in the inventive formulations are ethyl alcohol and isopropyl alcohol. High concentrations above about 35.0% and greater of alcohols are not preferred, as they disrupt the effectiveness of the formulations.

Auxiliary Ingredients

In some embodiments, the hair straightening formulations disclosed herein include one or more thickeners, particularly when the formulation is in the form of a cream, lotion or gel. In some embodiments, the thickeners include polyethylene glycol and/or sodium polyacrylate. In some embodiments, the thickener component is present in an amount of about 0.1-5.0% by weight of the formulations disclosed herein. More preferably, the thickener component is present in an amount of about 0.2-1.0% by weight of the formulations disclosed herein.

In some embodiments of the present invention, fragrances are added to mask the odor of various other components in the formulations of the present invention. In some embodiments, the fragrances are selected from the group consisting of: caramel, vanilla, coconut, and jasmine. One of skill in the art would readily appreciate that almost any fragrance could be used in the formulations of the present invention. In some embodiments, the fragrance component is about 0.1-10.0% by weight of the formulations disclosed herein. More preferably, the fragrance component is about 0.1-1.0% by weight of the formulations disclosed herein.

Product Application

In some embodiments, the present invention teaches a method in which a hair straightening formulation disclosed herein, or any component thereof, is applied to pre-cleaned, substantially dry, naturally curly hair, and distributed through the hair for a period sufficient to saturate the hair. The hair is then optionally styled by blow drying with a hand-held hair dryer or by another means with a substantially similar effect.

In some embodiments, the hair is washed with a shampoo that is slightly basic, before applying a formulation disclosed herein, or any component thereof. In some embodiments, the hair is washed with a shampoo that is slightly basic about 0.1-3.0 hours before applying the formulation. In some embodiments, the pH of the shampoo is about 7.0-8.0. In some embodiments, the shampoo contains citric acid buffered with sodium citrate. In some embodiments, alternative acids and/or buffers with substantially similar chemical effects are used.

When the above-mentioned methods of applying shampoo and treatment are used, the slightly alkaline pH swells the hair and breaks down the disulfide double bond of the cysteine portion of the keratin molecule. The porosity of the cuticle layer (the outer layer of the hair) is important since it determines the amount of treatment (fixative) agent that can subsequently enter the cortex of the hair.

In other embodiments of the present invention, the hair straightening formulation disclosed herein, or one or more components thereof, is (1) applied to pre-cleaned, optionally substantially dry, naturally curly hair, (2) distributed through the hair and maintained in contact with the hair for a period sufficient to saturate the hair, preferably at least about ten minutes, (3) optionally dried by blow drying the hair with a hand-held electric hair dryer or substantially equivalent means until the hair feels substantially dry to the touch and (4) styled with a heated ceramic flat hair iron having a platen, wherein temperature setting of the flat iron is in the range 150-235° C.

In certain embodiments, a preconditioning composition is applied to the hair, by spraying, brushing or equivalent means. The preconditioning composition is distributed through the hair, and maintained in contact with the hair for a period sufficient to saturate the hair. In certain embodiments, the preconditioning composition is applied and allowed to saturate the hair for at least about 5-10 minutes.

In some embodiments, the preconditioned hair is then rinsed with tepid water for at least about 30 seconds, towel blotted and then contacted with a hair straightening formulation.

The hair straightening formulations of the present invention, or one or more components thereof, are preferably applied with a brush, distributed through the hair, and maintained in contact with the hair for a period sufficient to saturate the hair. Preferably, the hair straightening formulation, or one or more components thereof, is in contact with the hair for at least about 5-10 minutes.

In some embodiments, the hair is then contacted with a thermal protectant composition distributed through the hair, the hair is then optionally blow-dried using a hand-held electric hair dryer or substantially equivalent means for drying, set at a heat of about 105° C. until the hair feels substantially dry to the touch, and is then styled with a heated ceramic flat hair iron having a platen temperature setting in the range 150-235° C. In some embodiments, the entire hair straightening process is completed in about 40-120 minutes.

In some embodiments of the present invention, the hair straightening formulation, or one or more components thereof, is present in the preconditioning composition, in the thermal protectant composition, or in the preconditioning composition and thermal protectant composition. In certain embodiments, neither a preconditioning composition nor thermal protectant composition are used, and the hair straightening formulation, or one or more components thereof, is applied directly to clean, damp hair.

In some embodiments, the preconditioning composition contains a cationic conditioning agent. In certain embodiments, the cationic conditioning agent is a monomeric or polymeric quaternary ammonium compound and is preferably alkaline in the presence of a curl minimizing agent. The thermal protectant compositions of the inventive method preferably contain a silicone component and are slightly acidic to substantially neutral in the presence of the hair straightening formulations, or components thereof.

In certain embodiments, the hair straightening system includes the use of at least one "leave-in" conditioner applied after the straightening procedure and left in the hair.

In certain embodiments, one or more of the reducing agents is applied before and separately from the remainder of the hair straightening formulation, or one or more components thereof. In some embodiments, this application is carried out to clean, damp hair and the solution is left in contact with the hair for about 5-30 minutes before applying the remainder of the hair straightening formulation, or one or more components thereof. In yet other embodiments, the pH-lowering agent is applied before and separately from the remainder of the hair straightening formulation, or one or more components thereof. In some embodiments, this application is carried out to clean, damp hair and the solution is left in contact with the hair for about 5-10 minutes before applying the remainder of the hair straightening formulation, or one or more components thereof. In yet other embodiments, the one or more pH lowering agents and one or more reducing agents are applied together, but separately from the remainder of the hair straightening formulation, or one or more components thereof.

The present invention is also directed to a kit with an intended function of facilitating the straightening of hair. The kit can be configured in numerous ways to be useful for practicing any of the inventive methods disclosed herein, including straightening hair with one or more of the inventive formulations, or one or more components thereof, disclosed herein.

The kit is an assemblage of materials or components, including at least one of the inventive formulations, or one or more components thereof. Thus, in some embodiments the kit contains a formulation including substances selected from the group consisting of: one or more keratin hydrolysates, one or more pH-lowering agents, one or more reducing agents, one or more crosslinking agents, and combinations thereof, with or without shampoo, conditioner, or other categories of additional components and/or agents described above and below.

In some embodiments, the kit is configured particularly for use with mammalian subjects. In some embodiments, the kit is configured particularly for use with human subjects.

Instructions for use may be included in the kit. "Instructions for use" typically include a tangible expression describing the technique to be employed in using the components of the kit to affect a desired outcome, including straightening hair with one or more of the formulations, or components thereof, as disclosed herein.

The materials and/or components assembled in the kit can be provided and stored in any convenient and suitable way that preserves their operability and utility. For example, the formulations, or one or more components thereof, can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as one or more of the inventive formulations and the like. The packaging material is constructed by well-known methods, preferably to provide a sterile, contaminant-free environment. As used herein, the term "package" refers to a suitable solid matrix or material such as glass, plastic, paper, foil, Styrofoam and the like, capable of holding the individual kit components. Thus, for example, a package can be a glass, plastic, or paper vessel used to contain suitable quantities of an inventive formulation containing hair straightener including: one or more keratin hydrolysates, one or more pH-lowering agents, one or more reducing agents, one or more crosslinking agents, and optionally one or more substances of the other categories of agents disclosed herein. The packaging material generally has an external label which indicates the contents and/or purpose of the kit and/or its components, as well as its various marketable attributes.

In some embodiments, the invention teaches a kit with components selected from the group consisting of: a hair straightening formulation, a thermal protectant composition, and combinations thereof. In some embodiments, the kit also contains one or more implements for performing a curl minimizing procedure. In certain embodiments, the implements are selected from the group consisting of: disposable gloves, a brush, a comb, a hand-held blow dryer, a flat hair iron, combinations thereof, and the like. The kit components preferably are separately packaged and contained in an outer package. The outer package can be a box or carton or shrink wrap, and preferably has instructional indicia printed thereon or visible therethrough.

Product and Method Promotion

In certain embodiments, the invention includes one or more forms of instructional indicia. In some embodiments of the present invention, instructional indicia are selected from the group consisting of: printed media, aural media, visual aids, electronic media, and combinations thereof, which instruct the user on the use of the hair product. In some embodiments of the present invention, printed media used with the formulations and accompanying products disclosed herein are selected from the group consisting of: labels attached to, or imprinted on, the components of the kit, package inserts, pamphlets, books, flyers, combinations thereof, and the like. In some embodiments of the present invention, aural media used with the formulations and accompanying products disclosed herein are selected from the group consisting of: tape recordings, audio compact discs, records, combinations thereof, and the like. In some embodiments of the present invention, visual aids used with the formulations and accompanying products disclosed herein are selected from the group consisting of: slides, movies, videos, DVDs, and the like. In some embodiments of the present invention, electronic media used with the formulations and accompanying products disclosed herein include electronic data storage media. In some embodiments, the electronic data storage media is selected from the group consisting of: diskettes, interactive CD-ROMs, interactive DVDs, combinations thereof, and the like.

While the foregoing written description of the invention enables one of ordinary skill to make and use what is considered presently to be the best mode thereof, those of ordinary skill will understand and appreciate the existence of variations, combinations, and equivalents of the specific embodiments, methods, and examples herein. The invention should therefore not be limited by the above described embodiments, methods, and examples, but by all embodiments and methods within the scope and spirit of the invention.

One skilled in the art will recognize many methods and materials similar or equivalent to those described herein, which could be used in the practice of the present invention. Indeed, the present invention is in no way limited to the methods and materials described.

The following examples are for illustrative purposes only and are not intended to limit the scope of the disclosure or its various embodiments in any way.

EXAMPLES

Example 1

Formulation #1

The hair straightening formulation may have the following composition:

| Ingredients | Weight % |
| --- | --- |
| keratin protein fraction | 0.5-2.0 |
| pH adjusting agent | 0.25-2.0 |
| crosslinking agent | 0.25-2.0 |
| reducing agent | 0.25-2.0 |
| propylene glycol | 1.0-5.0 |
| dimethicone | 0.25-1.0 |
| cyclomethicone | 0.5-2.0 |
| phenyl trimethicone | 0.5-2.0 |
| cetyl alcohol | 0.25-1.5 |
| cetrimonium chloride | 0.25-1.0 |
| glutamine | 0.25-1.0 |
| glycine | 0.25-1.0 |
| alanine | 0.25-1.0 |
| proline | 0.25-1.0 |
| serine | 0.25-1.0 |
| threonine | 0.25-1.0 |
| arginine | 0.25-1.0 |
| lysine | 0.25-1.0 |
| glutamic acid | 0.25-1.0 |
| silk amino acids | 0.25-2.0 |

| Ingredients | Weight % |
|---|---|
| *Mauritia flexuosa* (buriti) Fruit oil | 0.25-2.0 |
| *Cocos nucifera* (coconut) oil | 0.25-2.0 |

In order to apply the hair straightening formulation, the hair is thoroughly washed with a clarifying shampoo and towel-dried. The formulation is then applied to the damp hair, combed or brushed into the hair, and left to process for 20-30 min. The hair is then blow-dried thoroughly and then flat-ironed at 220° C.

Alternatively, the shampooed hair is dried fully with a hair drier. The formulation is then applied to the dry hair, combed or brushed into the hair, and left to process for 20-30 min. At that point, the hair can be rinsed out with water, dried thoroughly with a blow drier and then flat-ironed at 220° C. The processed hair can also be blow-dried thoroughly and then flat-ironed at 220° C., without the rinsing step.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

REFERENCES

1. Resnick, L.; Grams, I.; Goodfellow, A.; Allice, D. Hair Straightening Formulations, Methods, and Systems. US 2009/0165812 A1, Sep. 8, 2008.
2. Sycd, A. N.; Askar, N. A.; Milczarck, P. Keratin-protective Curl Minimizer Compositions, Method, and Kit Therefor. WO 2007/032762 A1, Sep. 12, 2005.
3. Whewell, C. S., The Chemistry of Hair. *J. Soc. Cosmetic Chem.* 1964, 15, 423-436.
4. Robbins, C. R., *Chemical and Physical Behavior of Human Hair* 3rd ed.: Springer-Verlag: 1994.
5. Cook; Smith, *Appl. Polym. Symp.* 1971, 18 (50), 663.
6. Parreira, H. C., On the Isoelectric Point of Human Hair. *J. Colloid Interface Sci.* 1980, 75 (1), 212-217.
7. Miyata, T.; Noishiki, Y. Medical Material. U.S. Pat. No. 4,695,281, Mar. 25, 1983.
8. Imamura, E.; Noishiki, Y.; Koyanagi, H.; Miyata, T.; Furuse, M. Bioprosthetic Valve. U.S. Pat. No. 5,080,670, Aug. 30, 1988
9. Harmalker, S.; Ash, K. Moisturizing Compositions. US 2007/0048235, Aug. 24, 2006.

10. King, K.; Chatterji, J. Foamed Acidizing Fluids, Additives and Methods of Acidizing Subterranean Zones U.S. Pat. No. 6,555,505, Apr. 29, 2003

11. Kelly, R. J.; Worth, G. H.; Roddick-Ianzilotta. A. D.; Rankin. D. A.; Ellis, G. D.; Mesman, P. J. R.; Summers. C. G.; Singleton, D. J. Production of Soluble Keratin Derivatives. U.S. Pat. No. 7,148,327, Jul. 17, 2002.

12. *International Cosmetic Ingredient Dictionary and Handbook.* 9th ed.; Cosmetic, Toiletry, and Fragrance Association: Washington D.C., 2002; Vol. 1-3.

13. 2001 *McCutcheon's Directories.* McCutcheon's Division, The Manufacturing Confectioner Publishing Co.: Glen Rock, N.J., 2001; Vol. 1-2.

14. DiBerardino. L., *CBR Cosmetic Bench Reference—Directory of Cosmetic Ingredients* 2005. Cosmetics and Toiletries, Allured Publishing Corporation: Carol Stream. Ill., 2005.

What is claimed is:

1. A composition comprising:
   at least one of a maleic acid, an ester of maleic acid, a maleimide, an N-substituted derivative of a maleimide, a maleamic acid, an N-substituted derivative of maleamic acid, a maleic anhydride, or a combination thereof, provided in an amount of about 1.0 wt. % to about 25.0 wt. %, based on the total weight of the composition; and
   a preservative comprising a glycerin containing compound or a plant-derived compound, provided in an amount of about 0.05 wt. % to 15 wt. % based on the total weight of the composition,
   wherein the composition has a pH of from 2.45 to 4.5.

2. The composition of claim 1, wherein the preservative comprises glycerin, ethylhexylglycerin, phenoxyethanol, or a combination thereof.

3. The composition of claim 1, wherein the preservative comprises grapefruit seed extract, radish root ferment filtrate, *Aloe barbadensis* leaf ferment filtrate, *Sorbus aucuparia* fruit ferment filtrate, *Ribes nigrum* fruit extract, *Sambucus nigra* fruit extract, *japonica* root extract, *Zingiber officinale* root extract, *Allium sativum* bulb extract, *Origanum vulgare* leaf extract, *Thymus vulgaris* leaf extract, *Rosmarinus officinalis* leaf extract, or a combination thereof.

4. The composition of claim 1, comprising at least one of maleic acid, an ester of maleic acid, maleic anhydride, or a combination thereof, and the preservative comprises phenoxyethanol or a plant-based preservative.

5. The composition of claim 1, comprising maleic acid and the preservative comprises phenoxyethanol.

6. The composition of claim 1, wherein the composition further comprises a reducing agent comprising an amine.

7. The composition of claim 6, wherein the amine comprises an amino acid.

8. The composition of claim 7, wherein the amino acid is lysine.

9. The composition of claim 1, further comprising an organic acid selected from the group consisting of tartaric acid, adipic acid, succinic acid, ascorbic acid, malonic acid, oxalic acid, pyruvic acid, picolinic acid, dipicolinic acid, citric acid, and a combination thereof.

10. The composition of claim 9, wherein the organic acid is citric acid.

11. The composition of claim 1, further comprising an emollient selected from the group consisting of sorbitol, glycerin, propylene glycol, ethylene glycol, polyethylene glycol, caprylyl glycol, polypropylene glycol, 1,3-butane diol, hexylene glycol, isoprene glycol, xylitol, and a combination thereof.

12. The composition of claim 11, wherein the emollient is propylene glycol.

13. The composition of claim 1, further comprising a surfactant, a keratin protein fraction, a botanical, and emulsifier, a skin-cleaning agent, a fragrance, a pre-conditioner, a thermal protectant, an aqueous-based diluent, or a combination thereof.

14. A method of treating hair, comprising:
   applying to a quantity of hair a composition comprising:
   at least one of maleic acid, an ester of maleic acid, a maleimide, an N-substituted derivative of maleimide, maleamic acid, an N-substituted derivative of maleamic acid, maleic anhydride, or a combination thereof, provided in an amount of about 1.0 wt.% to about 25.0 wt. %, based on the total weight of the composition; and
   a preservative provided in an amount of about 0.05 wt. % to 15 wt. %, based on the total weight of the composition,
   wherein the composition has a pH of from 2.45 to 4.5.

15. The method of claim 14, wherein the preservative comprises a glycerin containing compound or a plant-derived compound.

16. The method of claim 15, wherein the preservative comprises glycerin, ethylhexylglycerin, phenoxyethanol, or a combination thereof.

17. The method of claim 15, wherein the preservative comprises grapefruit seed extract, radish root ferment filtrate, *Aloe barbadensis* leaf ferment filtrate, *Sorbus aucuparia* fruit ferment filtrate, *Ribes nigrum* fruit extract, *Sambucus nigra* fruit extract, *japonica* root extract, *Zingiber officinale* root extract, *Allium sativum* bulb extract, *Origanum vulgare* leaf extract, *Thymus vulgaris* leaf extract, *Rosmarinus officinalis* leaf extract, or a combination thereof.

18. The method of claim 14, wherein the composition comprises at least one of maleic acid, an ester of maleic acid, maleic anhydride, or a combination thereof, and the preservative comprises phenoxyethanol or a plant-derived compound.

19. The method of claim 14, wherein the composition comprises maleic acid and the preservative comprises phenoxyethanol.

20. The method of claim 14, wherein the composition further comprises a reducing agent comprising an amine.

21. The method of claim 20, wherein the amine comprises an amino acid.

22. The method of claim 21, wherein the amino acid is lysine.

23. The method of claim 14, wherein the method does not impart any visibly undesirable coloration on the hair.

24. The method of claim 14, wherein the quantity of hair is substantially dry when the keratin-protectant composition is applied.

25. The method of claim 14, wherein the quantity of hair is wet when the composition is applied.

26. The method of claim 14, further comprising applying heat to the quantity of hair while the composition is applied to the hair.

27. The method of claim 26, wherein applying heat comprises heating the quantity of hair with a blow dryer.

28. The method of claim 26, wherein applying heat comprises heating the quantity of hair with a flattening iron.

* * * * *